(12) United States Patent
Bingaman et al.

(10) Patent No.: US 11,612,689 B2
(45) Date of Patent: Mar. 28, 2023

(54) INJECTOR SYSTEMS AND SYRINGE ADAPTERS FOR USE THEREWITH

(71) Applicant: BAYER HEALTHCARE LLC, Whippany, NJ (US)

(72) Inventors: Molly Bingaman, McCandless, PA (US); Erin Novickoff, Murrysville, PA (US); Patrick O'Rourke, New Middletown, OH (US); Stephen Schulte, Gibsonia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 173 days.

(21) Appl. No.: 17/095,450

(22) Filed: Nov. 11, 2020

(65) Prior Publication Data
US 2021/0069412 A1 Mar. 11, 2021

Related U.S. Application Data

(62) Division of application No. 16/478,793, filed as application No. PCT/US2018/014636 on Jan. 22, 2018, now Pat. No. 10,835,668.
(Continued)

(51) Int. Cl.
*A61M 5/145* (2006.01)
*A61M 5/315* (2006.01)
*A61M 5/142* (2006.01)

(52) U.S. Cl.
CPC ...... *A61M 5/14546* (2013.01); *A61M 5/1458* (2013.01); *A61M 5/31575* (2013.01);
(Continued)

(58) Field of Classification Search
CPC ............ A61M 5/31575; A61M 5/1458; A61M 5/14546; A61M 2005/14208;
(Continued)

(56) References Cited

U.S. PATENT DOCUMENTS 3,880,163 A 4/1975 Ritterskamp
4,006,736 A 2/1977 Kranys et al.
(Continued)

FOREIGN PATENT DOCUMENTS

EP 0346950 A2 12/1989
EP 0561122 A1 9/1993
(Continued)

OTHER PUBLICATIONS

"International Preliminary Report on Patentability from PCT Application No. PCT/US2018/014636", dated Aug. 8, 2019.
(Continued)

*Primary Examiner* — Bhisma Mehta
*Assistant Examiner* — Nidah Hussain
(74) *Attorney, Agent, or Firm* — David Schramm; James R. Stevenson; Joseph L. Kent

(57) ABSTRACT

An adapter for releasably attaching a syringe to an injector. The adapter comprises a mounting mechanism positioned at a rear end of the adapter to mount the adapter in a desired position relative to a front wall of the injector; and a syringe carrier section adapted to seat at least a portion of the syringe. The syringe carrier section defines a first opening on a top thereof to allow placement of the syringe therein from the top and a second opening in a rear section thereof to allow the drive member of the injector to communicate forward force to the plunger. A cover portion extends over a rearward end of the first opening and has a first end configured to abut the flange of the syringe when the syringe is positioned within the syringe carrier section.

20 Claims, 24 Drawing Sheets

Related U.S. Application Data

(60) Provisional application No. 62/547,257, filed on Aug. 18, 2017, provisional application No. 62/449,874, filed on Jan. 24, 2017.

(52) U.S. Cl.
CPC ............. *A61M 2005/14208* (2013.01); *A61M 2205/502* (2013.01); *A61M 2205/6018* (2013.01)

(58) Field of Classification Search
CPC .... A61M 2205/502; A61M 2205/6018; A61M 2205/60; A61M 2205/6081; A61M 5/2033; A61M 5/20; A61M 5/24; A61M 5/14216; A61M 5/145; A61M 5/30; A61M 5/31511; A61M 5/3234; A61J 1/2096
USPC ........................................................ 604/131
See application file for complete search history.

(56) References Cited

U.S. PATENT DOCUMENTS

| | | |
|---|---|---|
| 4,067,479 A | 1/1978 | Moline |
| 4,342,312 A | 8/1982 | Whitney et al. |
| 4,465,473 A | 8/1984 | Ruegg |
| 4,563,175 A | 1/1986 | Lafond |
| 4,650,465 A | 3/1987 | Langer et al. |
| 4,671,790 A | 6/1987 | Nishi |
| 4,677,980 A | 7/1987 | Reilly et al. |
| 4,695,271 A | 9/1987 | Goethel |
| 4,978,335 A | 12/1990 | Arthur, III |
| 5,026,349 A | 6/1991 | Schmitz et al. |
| 5,254,096 A | 10/1993 | Rondelet et al. |
| 5,269,762 A | 12/1993 | Armbruster et al. |
| 5,279,569 A | 1/1994 | Neer et al. |
| 5,300,031 A | 4/1994 | Neer et al. |
| 5,322,511 A | 6/1994 | Armbruster et al. |
| 5,383,858 A | 1/1995 | Reilly et al. |
| 5,456,670 A | 10/1995 | Neer et al. |
| 5,494,036 A | 2/1996 | Uber, III et al. |
| 5,520,653 A | 5/1996 | Reilly et al. |
| 5,535,746 A | 7/1996 | Hoover et al. |
| 5,545,140 A | 8/1996 | Conero et al. |
| 5,662,612 A | 9/1997 | Niehoff |
| 5,681,286 A | 10/1997 | Niehoff |
| 5,741,232 A | 4/1998 | Reilly et al. |
| 5,779,675 A | 7/1998 | Reilly et al. |
| 5,795,333 A | 8/1998 | Reilly et al. |
| 5,865,805 A | 2/1999 | Ziemba |
| 5,873,861 A | 2/1999 | Hitchins et al. |
| 5,899,885 A | 5/1999 | Reilly et al. |
| 5,913,844 A | 6/1999 | Ziemba et al. |
| 5,928,197 A | 7/1999 | Niehoff |
| 5,938,639 A | 8/1999 | Reilly et al. |
| 5,944,694 A | 8/1999 | Hitchins et al. |
| 5,947,929 A | 9/1999 | Trull |
| 5,997,502 A | 12/1999 | Reilly et al. |
| 6,080,136 A | 6/2000 | Trull et al. |
| 6,082,597 A | 7/2000 | Beckett et al. |
| 6,241,708 B1 | 6/2001 | Reilly et al. |
| 6,585,700 B1 | 7/2003 | Trocki et al. |
| 6,726,657 B1 | 4/2004 | Dedig et al. |
| 6,821,013 B2 | 11/2004 | Reilly et al. |
| 6,984,222 B1 | 1/2006 | Hitchins et al. |
| 7,018,363 B2 | 3/2006 | Cowan et al. |
| 7,273,477 B2 | 9/2007 | Spohn et al. |
| 7,419,478 B1 | 9/2008 | Reilly et al. |
| 7,497,843 B1 | 3/2009 | Castillo et al. |
| 7,691,085 B2 | 4/2010 | Dedig et al. |
| 8,317,099 B2 | 11/2012 | Perkins et al. |
| 8,849,318 B2 | 9/2014 | Olofsson et al. |
| 8,849,378 B2 | 9/2014 | Nemoto et al. |
| 8,882,702 B2 | 11/2014 | Suchecki et al. |
| 9,044,538 B2 | 6/2015 | Perkins et al. |
| 9,173,995 B1 * | 11/2015 | Tucker .............. A61M 5/14546 |
| 9,242,040 B2 | 1/2016 | Liscio et al. |
| 2001/0011163 A1 | 8/2001 | Nolan, Jr. et al. |
| 2003/0120212 A1 | 6/2003 | Dedig et al. |
| 2004/0210192 A1 | 10/2004 | Degentesh et al. |
| 2008/0200747 A1 | 8/2008 | Wagner et al. |
| 2011/0017859 A1 | 1/2011 | Vaughn et al. |
| 2012/0016234 A1 | 1/2012 | Nemoto et al. |
| 2013/0331691 A1 | 12/2013 | Uber, III et al. |
| 2015/0258278 A1 | 9/2015 | McLoughlin et al. |
| 2016/0058994 A1 | 3/2016 | Colman et al. |
| 2017/0056604 A1 * | 3/2017 | Cowan ................ A61M 5/1456 |
| 2017/0065763 A1 | 3/2017 | Rossitto et al. |

FOREIGN PATENT DOCUMENTS

| | | |
|---|---|---|
| EP | 0567186 A1 | 10/1993 |
| EP | 2939975 A1 | 11/2015 |
| JP | H08336592 A | 12/1996 |
| JP | H09122234 A | 5/1997 |
| JP | 1352034 | 2/2009 |
| JP | 4481582 B2 | 6/2010 |
| JP | 5864859 B2 | 2/2016 |
| WO | 9520410 A1 | 8/1995 |
| WO | 9526211 A1 | 10/1995 |
| WO | 9736635 A1 | 10/1997 |
| WO | 9910032 A1 | 3/1999 |
| WO | 0108727 A1 | 2/2001 |
| WO | 02056947 A1 | 7/2002 |
| WO | 2015142995 A1 | 9/2015 |
| WO | 2017091643 A1 | 6/2017 |

OTHER PUBLICATIONS

Liebel-Flarsheim company—Angiomat 6000 Digital Injection System Operator's Manual, 600950 Rev 1 (1990); p. 3-6 to 3-8, 4-52 to 4-56.

Liebel-Flarsheim Company, Angiomat 6000 Contrast Delivery System Brochure (1992).

Liebel-Flarsheim Company, Angiomat CT Digital Injection System Operator's Manual, 600964 (1990); pp. 1-3 to 1-4, 3-7 to 3-9, 4-37 to 4-39.

Liebel-Flarsheim Company, Angiomat CT Digital Injection System Operator's Manual, 600964 Rev. A (1991); pp. 1-5, 3-12, 4-48 to 4-51.

Liebel-Flarsheim Company, CT 9000 ADV Digital Injection System Manual, 800961-B, pp. 1-4 to 1-16 (Feb. 1998).

Mallinckrodt Optistar MR Digital Injection System, Operator's Manual, 801900-A (Nov. 1999).

Medrad MCT/MCT Plus Operation Manual, KMP 810P Revision B (1991), pp. 4-18 to 4-22 and 6-1 to 6-13.

MR Sonic Shot 50 Operator's Manual (with Accompanying English Translation of Chaper 11), Ver. 2.0.0 (Dec. 24, 1999).

U.S. Appl. No. 09/365,285, filed Jul. 30, 1999; never published or patented.

* cited by examiner

SECTION A-A

SECTION A-A

Add Contrast Type

- Contrast Name
- Concentration (mmol/ml)
- Vial Size (ml)
- Dosage (ml/kg)
- Dose Weight Limits (lbs)
- Dose minimum Age (Years)

Add New
- GADOVIST ×
- MAGNEVIST ×
- PRIMOVIST ×
- PROHANCE ×
- MAGNESCOPE ×
- MULTIHANCE ×

Is this contrast media sold by Eisai?
YES | NO

Cancel

FIG. 18B

INJECTOR SYSTEMS AND SYRINGE ADAPTERS FOR USE THEREWITH

CROSS REFERENCE TO RELATED APPLICATIONS

This application is a Divisional of U.S. application Ser. No. 16/478,793, filed Jul. 17, 2019, which is a § 371 national phase application of PCT International Application No. PCT/US2018/014636, filed Jan. 22, 2018, and claims priority to United States Provisional Patent Application Ser. No. 62/449,874, entitled "Injection Systems and Syringe Adapters for Use Therewith", filed Jan. 24, 2017 and 62/547,257, entitled "Systems and Methods for Fluid Delivery with an Adapter", filed Aug. 18, 2017, the contents of each of which are incorporated herein by reference, in their entirety.

BACKGROUND OF THE DISCLOSURE

Field

The present disclosure relates to powered injector systems and syringe adapters for use therewith.

Description of Related Art

In many medical diagnostic and therapeutic procedures, a physician or other person injects a patient with a fluid. In recent years, a number of injector-actuated syringes and powered injectors for pressurized injection of fluids, such as contrast media, have been developed for use in procedures such as angiography, computed tomography, ultrasound, nuclear medicine, NMR/MRI, and other imaging modalities. In general, these powered injectors are designed to deliver a preset amount of contrast media at a preset flow rate.

Typically, such powered injectors include a housing allowing one or more syringes to be connected to a front wall thereof. These injectors further comprise drive members such as pistons that connect to a syringe plunger. A syringe used with a front-loading injector usually includes a readily releasable mounting mechanism for securing the syringe to the front wall of the injector. Such syringes may, for example, include a syringe body, a plunger reciprocally mounted therein, and a plunger extension for transfer of force to the plunger.

Accordingly, adapters have been designed to allow the use of various syringes with a front-loading injector. For instance, an adapter may include a syringe carrier having a front end, a rear end, and a syringe retaining channel located between the carrier front and rear ends for engaging at least a portion of the syringe flange. Mounting flanges near the rearward end of the carrier releasably mount the carrier in a desired position relative to the front wall of the injector.

Although such conventional adapters provide a substantial improvement in the art, it remains desirable to develop improved adapters for use with syringes of various types to permit use of such syringes with front-loading injectors.

In addition, the need to select and install these adapters to an injector prior to performing an injection increases the time required and complexity of each procedure. In particular, users must determine which adapters are approved for use with different types of prefilled syringes. Different adapters may also have different use parameters, meaning that certain injection parameters or injector settings may need to be adjusted each time that a new adapter is selected. Users may be responsible for manually adjusting these parameters and settings each time that a new adapter is used.

For these reasons, it is desirable to develop user interface systems for guiding users through the injector setup process and, in particular, for providing assistance in selecting and installing different types of adapters. The user interfaces and injector systems disclosed herein are intended to provide such benefits.

SUMMARY

In accordance with one aspect of the present disclosure, provided is an adapter for releasably attaching a syringe to an injector. The syringe comprises a body, a front end having a fluid outlet extending from a forward end of the body, a plunger slideably positioned within the body, and a flange extending around a rearward end of the body. The injector comprises a front wall, an opening formed in the front wall, and a drive member reciprocally mounted in the injector. The adapter comprises a mounting mechanism positioned at a rear end of the adapter to mount the adapter in a desired position relative to the front wall of the injector; and a syringe carrier section adapted to seat at least a portion of the syringe. The syringe carrier section defines a first opening on a top thereof to allow placement of the syringe therein from the top and a second opening in a rear section thereof to allow the drive member of the injector to communicate forward force to the plunger. A cover portion extends over a rearward end of the first opening and has a first end configured to abut the flange of the syringe when the syringe is positioned within the syringe carrier section.

A forward portion of the syringe carrier section may comprise two substantially opposed shoulder portions. The opposed shoulder portions may be configured to abut the front end of the syringe so that the force exerted by the syringe on the adapter during an injection is generally symmetrical about an axis of the adapter. The two substantially opposed shoulder portions may be positioned on a first lateral side and a second lateral side, respectively, of the syringe carrier section.

The adapter may further comprise an intermediate section operably connected to and disposed between the syringe carrier section and the mounting mechanism. A push rod may be at least partially disposed within the intermediate section. The push rod may comprise a first end for engaging the plunger of the syringe and a second end. The second end of the push rod may comprise a pair of biased engagement legs that are configured to engage the drive member of the injector. Each of the engagement legs may be biased by a spring element to return to an engagement position. Each of the engagement legs may comprise a free first end and a second end that is connected to the push rod. The free first end of each of the engagement legs may comprise a gripping member configured to engage a flange provided on the drive member of the injector.

In certain examples, a sealing member may be positioned within the second opening of the syringe carrier section and configured to contact the push rod and prevent a fluid from the syringe from passing rearward of the sealing member. A second end of the cover portion may comprise a retainer ring extending therefrom to hold the sealing member in place within the second opening of the syringe carrier section.

The syringe carrier section may comprise an inner surface and a flexing retaining member disposed on the inner surface. The flexing retaining member may be adapted to place pressure on at least one side of the syringe to retain the syringe within the syringe carrier section. The at least one flexing retaining member may comprise a first leg having a first end operatively connected to the inner surface of the syringe carrier section and a second free end, and a second leg spaced from the first leg having a first end operatively connected to the inner surface of the syringe carrier section and a second free end such that a space between the first leg and the second leg may be configured to receive the syringe.

In accordance with another aspect of the present disclosure, provided is an adapter for releasably attaching a syringe to an injector. The syringe comprises a body, a front end having a fluid outlet extending from a forward end of the body, a plunger slideably positioned within the body, and a flange extending around a rearward end of the body. The injector comprises a front wall, an opening formed in the front wall, and a drive member reciprocally mounted in the injector. The adapter comprises: a mounting mechanism positioned at a rear end of the adapter to mount the adapter in a desired position relative to the front wall of the injector; a syringe carrier section adapted to seat at least a portion of the syringe; and a cover portion extending over a rearward end of the first opening. The syringe carrier section defines a first opening on a top thereof to allow placement of the syringe therein from the top and a second opening in a rear section thereof to allow the drive member of the injector to communicate forward force to the plunger. The cover portion comprises a body having a front face and rear face that are angled to meet at a top of the body. The front face of the cover portion causes the syringe to pivot in a controlled manner during removal of the syringe from the syringe carrier section.

The adapter may further comprise an intermediate section operably connected to and disposed between the syringe carrier section and the mounting mechanism and a push rod at least partially disposed within the intermediate section. The push rod may comprise a first end for engaging the plunger of the syringe and a second end. The second end of the push rod may comprise a pair of biased engagement legs that are configured to engage the drive member of the injector. Each of the engagement legs may be biased by a spring element to return to an engagement position. Each of the engagement legs may comprise a free first end and a second end that is connected to the push rod. The free first end of each of the engagement legs may comprise a gripping member configured to engage a flange provided on the drive member of the injector.

A first end of the cover portion may be configured to abut the flange of the syringe when the syringe is positioned within the syringe carrier section. A sealing member may be positioned within the second opening of the syringe carrier section and may be configured to contact the push rod and prevent a fluid from the syringe from passing rearward of the sealing member. A second end of the cover portion may comprise a retainer ring extending therefrom to hold the sealing member in place within the second opening of the syringe carrier section.

The syringe carrier section may comprise an inner surface and a flexing retaining member disposed on the inner surface. The flexing retaining member may be adapted to place pressure on at least one side of the syringe to retain the syringe within the syringe carrier section. The at least one flexing retaining member may comprise a first leg having a first end operatively connected to the inner surface of the syringe carrier section and a second free end, and a second leg spaced from the first leg having a first end operatively connected to the inner surface of the syringe carrier section and a second free end such that a space between the first leg and the second leg may be configured to receive the syringe.

In accordance with still a further aspect of the present disclosure, a feedback and control system for a fluid injector includes an injector comprising a control device and at least one syringe port configured to receive a syringe adapter. The at least one syringe port comprises a sensor for obtaining information about the syringe adapter mounted thereto. The control device is in electronic communication with the injector and includes a visual display. The control device displays a user interface for guiding a user during operation of the injector. The control device is configured to: determine a recommended adapter type based on a type of fluid to be injected to a patient; determine one or more injection parameters for an injection to be performed based, at least in part, on the recommended adapter type; confirm that the syringe adapter mounted to the syringe port is the recommended adapter type; and display a notification on the visual display if the syringe adapter mounted to the syringe port is not the recommended adapter type.

According to another aspect of the disclosure, a feedback and control system for a fluid injector includes an embodiment of the injector and the control device. The injector comprises at least one syringe port configured to receive a syringe adapter. The at least one syringe port comprises an axially movable piston configured to engage a plunger of a prefilled syringe inserted in the adapter and a sensor for obtaining information about a syringe and/or adapter mounted to the syringe port. The control device is in electronic communication with the injector and comprises a visual display. The control device displays a user interface for guiding a user during operation of the injector. The control device is configured to: provide a visual representation of a syringe on the visual display; cause the piston of the syringe port to advance from a home position through the syringe adapter mounted to the syringe port towards a plunger of the prefilled syringe; update the visual representation of the syringe to depict that the syringe is full of fluid as the piston begins to advance past the home position; and further update the visual representation of the syringe on the visual display to display a volume of fluid remaining in the syringe, wherein the displayed volume of fluid remaining in the syringe is determined based on a position of the piston relative to the home position of the piston.

According to another aspect of the disclosure, a feedback and control system for a fluid injector includes an embodiment of the injector and the control device. The injector comprises at least one syringe port configured to receive a syringe adapter. The at least one syringe port comprises a sensor for obtaining information for the adapter. The control device in electronic communication with the injector comprises a visual display. The control device displays a user interface for guiding a user during operation of the injector. The control device is configured to: receive information from the syringe port sensor to identify a type of adapter connected to the at least one syringe port; and provide on the visual display a visual icon indicating the type of the adapter connected to the at least one syringe port. The visual icon comprises a visual representation of an adapter, which identifies the type of adapter.

In accordance with yet another aspect of the disclosure, provided is an adapter for releasably attaching a shielded syringe to an injector. The shielded syringe comprises a body, a front end having a fluid outlet extending from a forward end of the body, a plunger slideably positioned within the body, a flange extending around a rearward end of the body, and a syringe shield covering at least a portion of the syringe body. The injector comprises a front wall, an opening formed in the front wall, and a drive member reciprocally mounted in the injector. The adapter comprises: a mounting mechanism positioned at a rear end of the adapter to mount the adapter in a desired position relative to the front wall of the injector; a syringe carrier section adapted to seat at least a portion of the syringe; an insert member provided at a forward portion of the syringe carrier section; and an intermediate section operably connected to and disposed between the syringe carrier section and the mounting mechanism. The syringe carrier section defines a first opening on a top thereof to allow placement of the syringe therein from the top and a second opening in a rear section thereof to allow the drive member of the injector to communicate forward force to the plunger. The insert member is designed and configured to securely hold the shielded syringe therein.

The insert member may comprise a pair of notches provided to secure the flange of the shielded syringe therein. A forward force during an injection procedure on the shielded syringe from the drive member of the injector may be one of fully transmitted through the syringe shield, partially transmitted through the syringe shield, and prevented from being transmitted through the syringe shield.

In accordance with still another aspect of the disclosure, provided is an adapter for releasably attaching a syringe to an injector. The syringe comprises a body, a front end having a fluid outlet extending from a forward end of the body, a plunger slideably positioned within the body, and a flange extending around a rearward end of the body. The injector comprises a front wall, an opening formed in the front wall, and a drive member reciprocally mounted in the injector. The adapter comprises: a mounting mechanism positioned at a rear end of the adapter to mount the adapter in a desired position relative to the front wall of the injector; a syringe carrier section adapted to seat at least a portion of the syringe; and an intermediate section operably connected to and disposed between the syringe carrier section and the mounting mechanism. The syringe carrier section defining a first opening on a top thereof to allow placement of the syringe therein from the top. The intermediate section comprises a reduction mechanism to modify a displacement relationship between the drive member of the injector and the plunger of the syringe.

The reduction mechanism may comprise: a generally planar element having a top surface and a bottom surface and a slot extending therebetween; a plunger engaging mechanism extending through the slot and configured to engage the plunger of the syringe prior to an injection procedure; a pair of rails extending from the bottom surface of the generally planar element; a drive member engaging portion positioned to engage the drive member of the injector and travel along the rails during an injection procedure; a lever having a first end pivotally connected to the drive member engaging portion, a second end pivotally connected to the bottom surface of the planar element, and an intermediate portion; and a slider mechanism located centrally on the bottom surface of the planar element. The slider mechanism may be pivotally connected to the intermediate portion of the lever and operatively connected to the plunger rod engaging mechanism such that movement of the slider mechanism causes the plunger to move through syringe and expel fluid therefrom.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

BRIEF DESCRIPTION OF THE DRAWINGS

FIG. 16 is a schematic drawing of another user interface screen for an injector system in accordance with the present disclosure;

FIG. 17 is a schematic drawing of another user interface screen for an injector system in accordance with the present disclosure;

FIGS. 18A and 18B are schematic drawings of additional user interface screens for an injector system in accordance with the present disclosure;

DESCRIPTION

Figure 1:
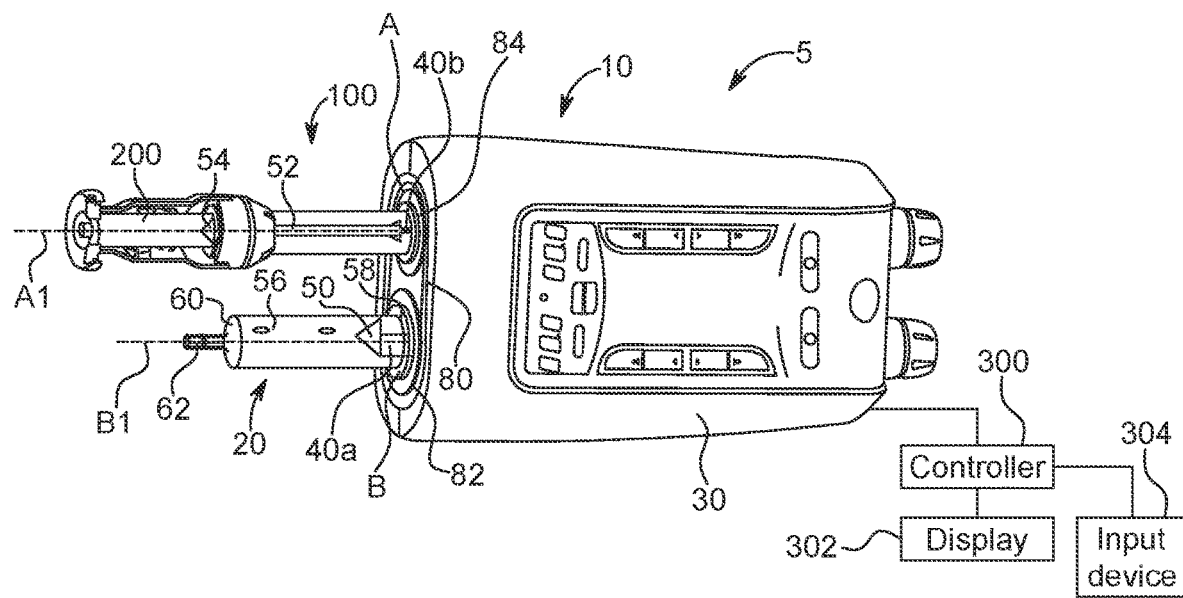
FIG. 1 is a perspective view of an injector system in accordance with the present disclosure for use in connection with an MRI procedure.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

The adapter of the present disclosure can be used in connection with virtually any injector and any syringe that is not specifically designed for use with the injector (i.e., a "non-native syringe") or syringe portion simply by appropriate design of the injector interface mounting mechanism, injector interface section, or injector interface portion of the adapter and appropriate design of the syringe interface portion of the adapter. The adapter may enable an injector designed for one use with one or more imaging modalities, for example CT or MR, to be used with another imaging modality, for example nuclear medicine, by accommodation a syringe and a shield as are commonly used with radioactive fluids for injection. In that regard, the syringe adapters of the present disclosure include a forward portion that includes a syringe interface to interact with and connect to the non-native syringe or syringe portion and a rearward portion that includes an injector interface to operatively connect the adapter to the syringe interface of the injector. The injector interface generally has a conformation similar to the mounting mechanism (for example, a flange configuration) found on syringes designed for use with the injector (i.e., "native syringes") (through which such native syringes are attached to the syringe interface of the injector).

With reference to FIG. 1, an exemplary front-loading injector system 5 is illustrated. Injector system 5 is particularly adapted for use in MRI procedures and includes a powered injector 10, a native syringe 20 for injection of saline solution, and an adapter 100. An example of an injector 10 is the Medrad® MRXperion™ MR Injection System available from the Radiology business of the Pharmaceutical Division of Bayer AG of Indianola, Pa., U.S.A. However, the adapter disclosed herein may be used in connection with other fluid delivery systems, including injectors and infusion pumps for computed tomography, ultrasound, angiographic procedures, nuclear medicine, and other imaging procedures.

The injector 10 comprises an injector housing 30 comprising a first drive member or injector piston 40a therein which cooperates with a syringe plunger 50 in native syringe 20 to inject a fluid from the interior of native syringe 20 into a patient. The injector 10 also includes a second drive member 40b that cooperates with a push rod 52 of the adapter 100 and, in turn, a plunger 54 of a non-native syringe 200. In one arrangement, the native syringe 20 may contain saline and the non-native syringe 200 may contain a fluid such as a contrast medium.

As used herein to describe injector system 5, the terms "axial" or "axially" refer generally to, for example, an axis A1 around which adapter 100 is formed (although not necessarily symmetrically therearound) or an axis B1 around which native syringe 20 is formed (although not necessarily symmetrically therearound). The terms "proximal" or "rearward" refer generally to an axial or a longitudinal direction toward the end of injector housing 30 opposite the end to which the native syringe 20 and adapter 100 are mounted. The terms "distal" or "forward" refer generally to an axial or a longitudinal direction toward a syringe tip of the native syringe 20 or the non-native syringe 200. The term "radial" refers generally to a direction normal to an axis such as axis A1 or axis B1.

The native syringe 20 and the adapter 100 are, in one example, removably connected to the injector 10. In that regard, injector 10 includes a front wall 80 having a first syringe port or opening 82 formed therein, referred to herein as syringe port B. The drive member 40a is reciprocally mounted within the injector 10 and is extendible through opening 82. As described in U.S. Pat. No. 6,652,489, which is hereby incorporated by reference in its entirety, the native syringe 20 includes a body or barrel portion 56 having a rear end 58 and a front end 60 including a fluid discharge or outlet 62. A mounting flange (not shown) is associated with barrel portion 56 adjacent to or at rear end 120 of syringe 20. In addition, a flange (sometimes referred to as a drip flange) is positioned forward of the mounting flange to, for example, facilitate the engagement of syringe 20 to the first opening 82 of the injector and/or to prevent fluid expelled from discharge or outlet 62 of syringe 20 from entering into injector 10 via the first opening 82. In one example, the first opening 82 has a syringe interface (not shown) which cooperates with the mounting flange of the syringe 20.

Figure 2:
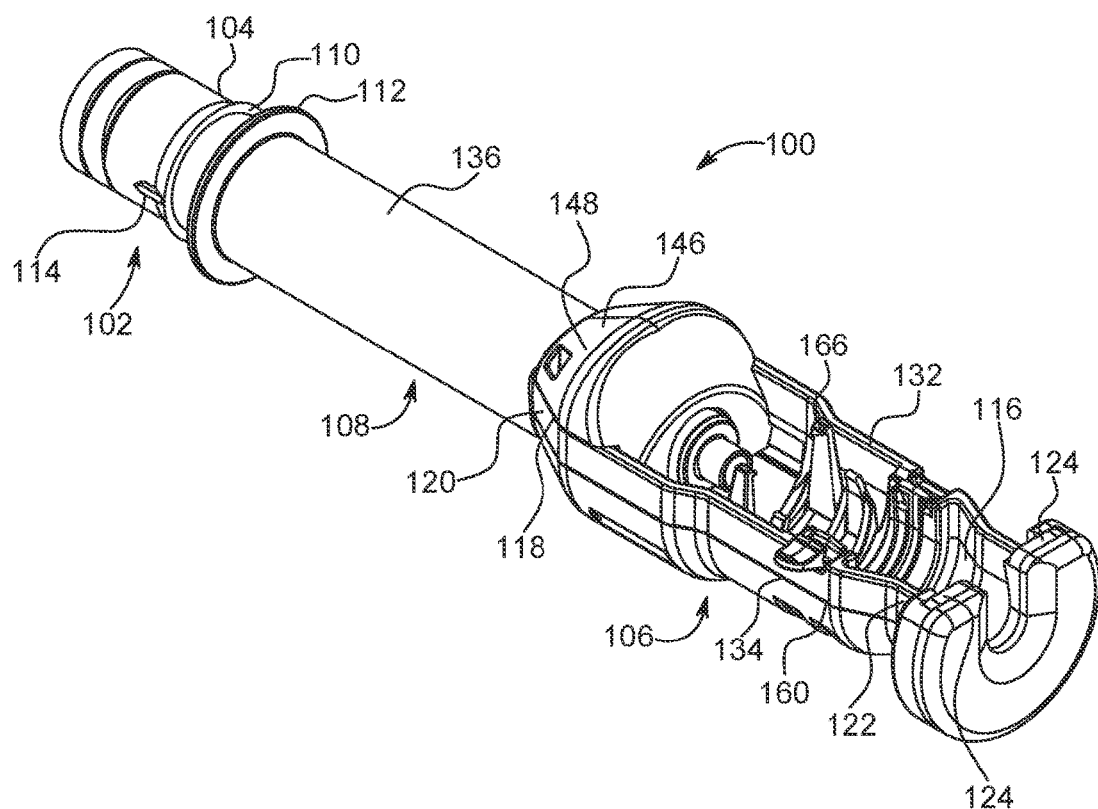
FIG. 2 is a perspective view of an adapter for use with the injector system of FIG. 1 in accordance with the present disclosure.
Figure 3:
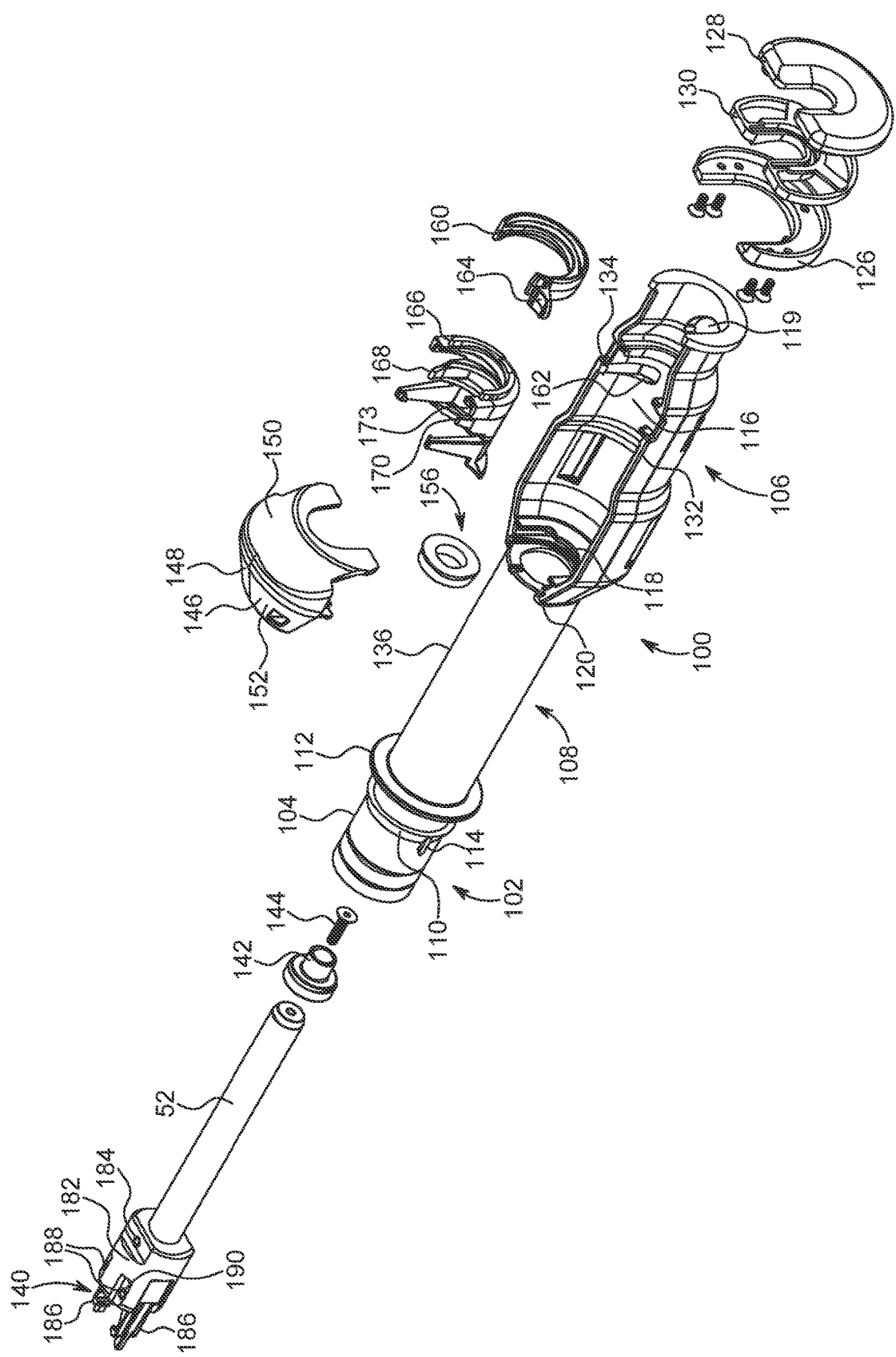
FIG. 3 is an exploded perspective view of the adapter of FIG. 2.
Figure 4:
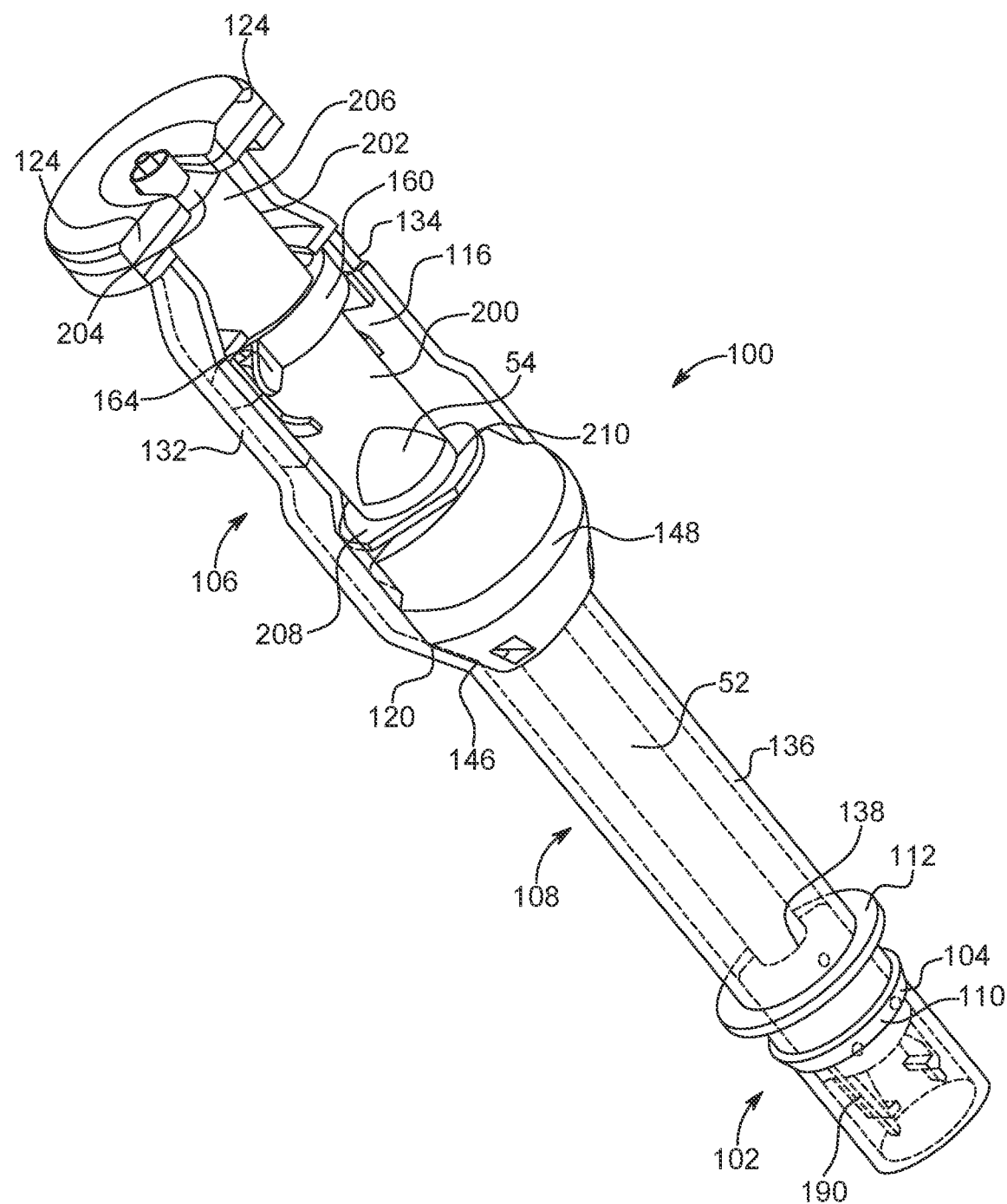
FIG. 4 is a perspective view of the adapter of FIG. 2 with a syringe loaded therein.

The front wall 80 of the injector 10 further includes a second syringe port or opening 84 formed therein, referred to herein as syringe port A. The drive member 40b is reciprocally mounted within the injector 10 and is extendible through the second opening 84. With reference to FIGS. 2-4 and with continued reference to FIG. 1, the adapter 100 is configured to releasably attach the non-native syringe 200 to the second opening 84 of the injector 10. A typical non-native syringe 200 comprises a cylindrical body 202, a front end 204 extending from a forward end 206 of the body 202, a plunger 54 slideably positioned within the body 202, and a flange 208 extending around a rearward end 210 of the body 202 (see FIG. 4). The front end 204 may be of any angle, positive or negative, or any other curvature and includes a fluid outlet.

In one example, the adapter 100 comprises: a mounting mechanism 102 positioned at a rear end 104 of the adapter 100 to mount the adapter 100 in a desired position relative to the front wall 80 of the injector 10; a syringe carrier section 106 adapted to seat the syringe 200 therein; and an intermediate section 108 operably connected to and disposed between the syringe carrier section 106 and the mounting mechanism 102.

The mounting mechanism 102 comprises any suitable mechanism for releasably mounting the adapter 100 to the syringe interface within the second opening 84. In one example, the mounting mechanism 102 comprises a mounting flange 110 and a drip flange 112 positioned forward of the mounting flange 110 to, for example, facilitate the engagement of the adapter 100 to the second opening 84 of the injector and/or to prevent fluid expelled from the syringe 200 from entering into injector 10 via the second opening 84.

As rear end 104 of the adapter 100 is passed through the second opening 84 of the front wall 80 of the injector 10, the mounting flange 110 contacts the syringe interface positioned therein. Mounting flange 110 includes a sloping section and a shoulder section that is essentially perpendicular to the exterior surface of the cylindrical rear end 104 of the adapter 100. The syringe interface is adapted to engage a forward surface or shoulder of mounting flange 110 of adapter 100 when the adapter 100 is fully installed in the second opening 84. At least one, and desirably two or more, extending tabs or projections 114 are provided at rear end 104 of adapter 100. Upon rotation of the adapter 100, tabs or projections 114 enable release of adapter 100 from engagement with the syringe interface. This mounting mechanism is similar to the mounting mechanism for a syringe disclosed in International Patent Application Publication No. WO 2015/142995, which is hereby incorporated by reference. While one example of a mounting mechanism is described hereinabove, this is not to be construed as limiting the present disclosure as any suitable mounting mechanism may be utilized to releasably attach the adapter 100 to the front wall 80 of the injector 10, such as the mounting mechanisms disclosed in U.S. Pat. Nos. 6,726,657 and 9,173,995, which are hereby incorporated by reference.

The syringe carrier section 106 defines a first opening 116 on a top thereof to allow placement of the syringe 200 therein from the side and a second opening 118 in a rear section 120 thereof to allow the drive member 40a of the injector to communicate forward force to the plunger 54 of the syringe 200. A forward portion 122 of the syringe carrier section 106 comprises two substantially opposed shoulder portions 124. In one example, the opposed shoulder portions 124 are configured to abut the front end 204 of the syringe 200 so that the force exerted by the syringe 200 on the adapter 100 during an injection is generally symmetrical about the axis A1 of the adapter 100. The opposed shoulder portions 124 may be formed from a first substantially U-shaped clamping element 126 and a second substantially U-shaped clamping element 128 having a resilient bumper 130 interposed therebetween such that the two substantially opposed shoulder portions 124 are positioned on a first lateral side 132 and a second lateral side 134, respectively, of the syringe carrier section 106. In addition, a third opening 119 is provided in a bottom of the forward portion 122 of the syringe carrier section 106. This third opening 119 allows a user to eject the syringe 200 from the syringe carrier section 106 once an injection procedure is complete.

Because the top portion of the syringe carrier section 106 and the opposed shoulder portions 124 are open for ease of removal of syringe 200, asymmetrical loading of mounting mechanism 102 can occur if front end 204 of syringe 200 contacts a bottom portion of the shoulder portions 124 during advancement of push rod 52. The resulting bending moment about mounting mechanism 102 can cause failure of the adapter 100. To substantially reduce or eliminate asymmetrical loading, shoulder portions 124 are shaped, in one example, to prevent such asymmetrical loading by, for example, being open on the top and bottom thereof. Removing a bottom edge of shoulder portions 124 where front end 204 of syringe 200 would otherwise rest results in generally symmetrical loading about the axis of the adapter system 100 (and syringe 200) and substantially reduces or removes lateral loads and bending moments during forward plunger advancement. Axial load applied to the end of adapter 100 is maximized while lateral load is minimized.

The intermediate section 108 is operably connected to and disposed between the syringe carrier section 106 and the mounting mechanism 102. The intermediate section 108 comprises a cylindrical body 136 having the push rod 52 at least partially disposed therein. In one example, the push rod 52 has a first end for engaging the plunger 54 of the syringe 200 and a second end 138. The second end 138 of the push rod 52 includes an engagement mechanism 140 configured to engage the drive member 40b of the injector 10. The first end of the push rod 52 includes an element 142 configured to releasably connect the push rod 52 to the plunger 54. The element 142 may be integrally formed with the push rod 52 or connected thereto with a bolt 144 or other suitable fastening mechanism.

Figure 5:
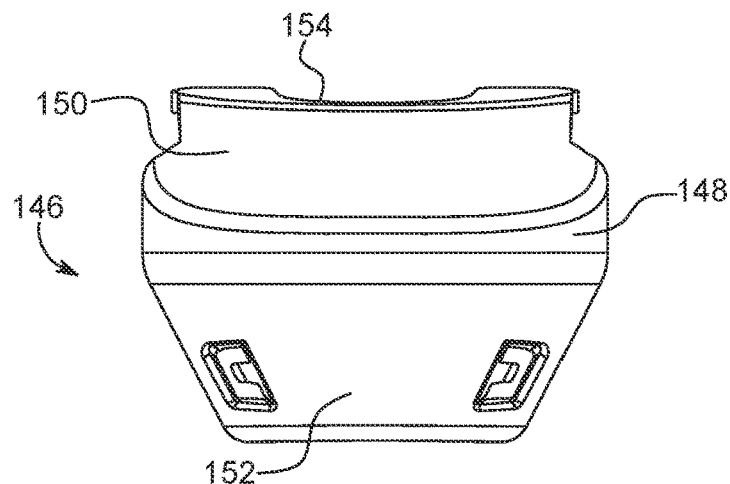
FIG. 5 is a perspective view of a cover portion of the adapter of FIG. 2.
Figure 6:
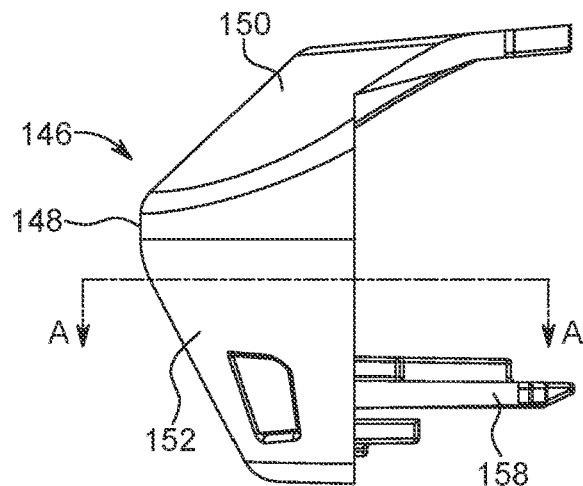
FIG. 6 is a side view of the cover portion of FIG. 5.
Figure 7:
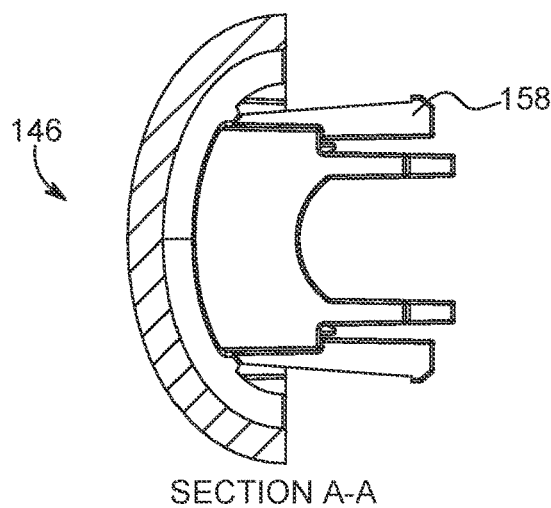
FIG. 7 is a cross-sectional view of the cover portion taken along line A-A in FIG. 6.

With reference to FIGS. 5-7 and with continued reference to FIGS. 2-4, the syringe carrier section 106 is provided with a cover portion 146 extending over a rearward end of the first opening 116. The purpose of the cover portion 146 is to protect an operator's hands from entering the area where the push rod 52 engages the syringe 200 during operation. The cover portion 146 may also be configured to prevent an incompatible syringe from fitting in the adapter 100, as some adapters are sized (e.g., having a unique height or other dimensions) to accommodate or receive only certain types of compatible syringes. The cover portion 146 has a body 148 that is sized and shaped to fit over the rearward end of the first opening 116. The body 148 includes a front face 150 and a rear face 152 that are angled to meet at the top of the body 148. A forward end of the front face 150 of the body 148 is configured to abut the flange 208 of the syringe 200 when the syringe 200 is positioned within the syringe carrier section 106 and has a semicircular cutout 154 that allows the push rod 52 to pass therethrough. By abutting the flange 208 of the syringe 200, the cover portion 146 biases the syringe 200 toward the forward portion 122 of the syringe carrier section 106, thereby encouraging forward biased insertion of the syringe 200. Forward biasing of the syringe 200 aids with the action of priming the syringe 200 by eliminating additional forward movement of the syringe 200 which may cause unintended fluid ejection/waste of contrast. In addition, cover portion 146 allows for easier removal of the syringe 200 following an injection procedure. Due to the angled front face 150 of the cover portion 146, the syringe 200 pivots in a more controlled manner when a user presses on the syringe 200 through the third opening 119 to eject the syringe 200 from the syringe carrier section 106.

The adapter 100 also includes a cleaning or contact member such as a wiper seal 156 positioned within the second opening 118 of the syringe carrier section 106. The wiper seal 156 has a substantially ring-like shape that allows the push rod 52 to extend therethrough. An end of the rear face 152 of the cover portion 146, in one example, includes a retainer ring structure 158 extending therefrom to hold the wiper seal 156 in place within the second opening 118 of the syringe carrier section 106. The wiper seal 156 operates to remove unwanted contrast media (resulting, for example, from leakage and/or spillage) from the push rod 52. In that regard, as the drive member 40b of the injector 10 is being retracted following an injection, wiper seal 156 cleans/wipes any contrast media that has inadvertently adhered to push rod 52 therefrom. Moreover, wiper seal 156 also minimizes unwanted contrast media from entering the intermediate section 108 of the adapter system 100. The retaining ring structure 158, in one example, holds wiper seal 156 in place via a pressure fit in the second opening 118 of the syringe carrier section 106.

The syringe carrier section 106 may further be provided with one or more features to secure the syringe 200 at a desired orientation within the first opening 116 thereof. For example, the adapter 100 may include a rotating retaining member 160 to assist in retaining and/or stabilizing syringe 200 in proper alignment within the first opening 116 of the syringe carrier section 106. The rotating retaining member 160 is slideably retained in a generally cylindrically shaped passage 162 in the syringe carrier section 106 (see FIG. 3). The rotating retaining member 160 is illustrated in an open or disengaged position in FIG. 2. To close or engage the rotating retaining member 160 to retain syringe 200, the operator can supply force to collar tab 164 to rotate retaining member 160 within passage 162 to a closed position as illustrated in FIG. 4. In some examples, the rotating retaining member 160 is brightly colored to provide user feedback to promote use and closure of the rotating retaining member 160.

Figure 8:
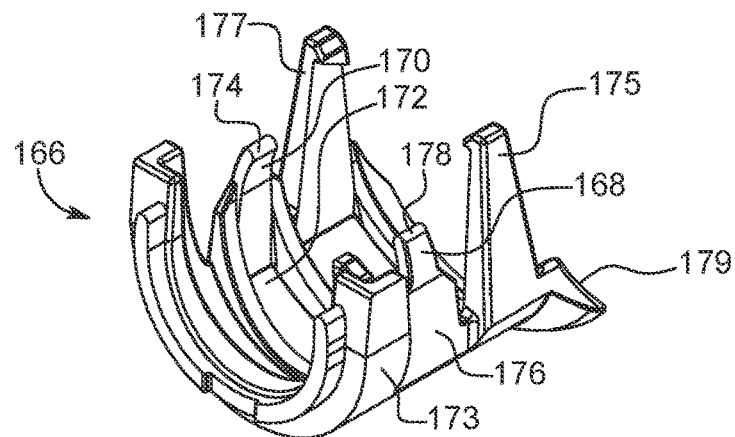
FIG. 8 is a perspective view of a flexing retaining member of the adapter of FIG. 2.
Figure 9:
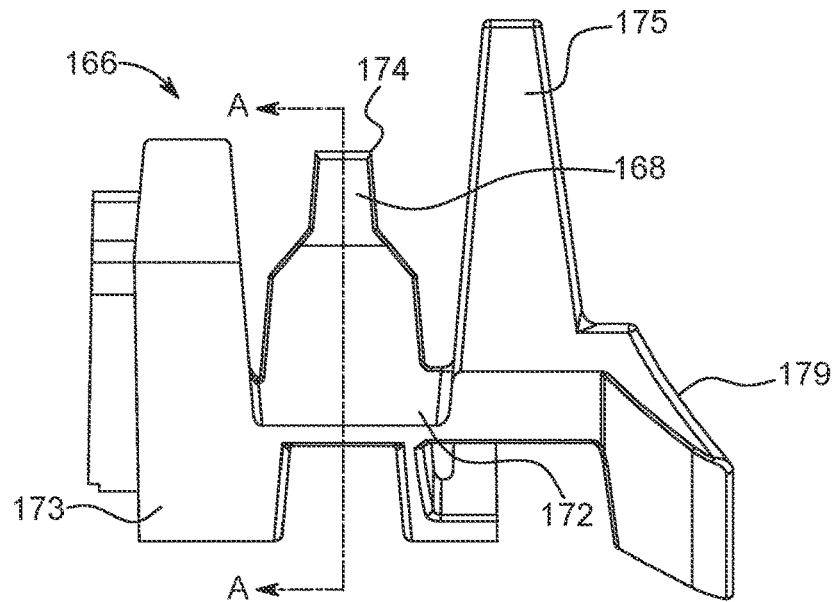
FIG. 9 is a side view of the flexing retaining member of FIG. 8.
Figure 10:
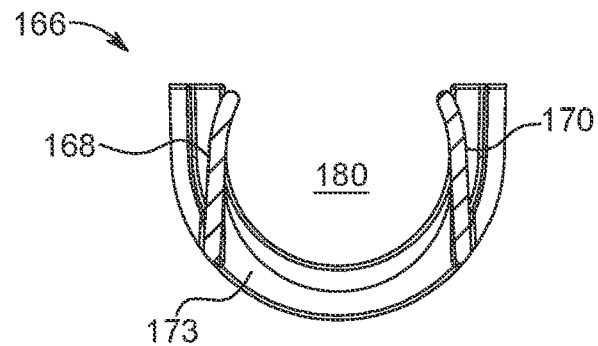
FIG. 10 is a cross-sectional view of the flexing retaining member taken along line A-A in FIG. 9.

With reference to FIGS. 8-10 and with continuing reference to FIGS. 2-4, the syringe carrier section 106 may also include a flexing retaining member 166 disposed on an inner surface thereof. The flexing retaining member 166 is adapted to place pressure on at least one side of the syringe 200 to retain the syringe 200 within the syringe carrier section 106. In one example, the flexing retaining member 166 includes a first leg 168, a second leg 170, and a body portion 173 operatively connected to the inner surface of the syringe carrier member 106. The first leg 168 has a first end 172 extending from the body portion 173 and a second free end 174. The second leg 170 also has a first end 176 and a second free end 178. The second leg 170 is spaced from the first leg 168 such that a space 180 between the first leg 168 and the second leg 170 is configured to receive the syringe 200. The flexing retaining member 166 assists, for example, in retaining the syringe 200 within syringe carrier section 106 when the injector 10 is rotated to a position other than horizontal when syringe 200 is placed with the syringe carrier section 106. In one example, if the injector 10 is in a vertical orientation, the flexing retaining member 166 prevents the syringe 200 from falling out of syringe carrier section 106 even before the rotating retaining member 160 can be rotated to a closed position. The flexing retaining member 166 is more durable than previous designs, thereby allowing for longer use. Specifically, the first and second legs 168, 170 are optimized in thickness and material for repeated installations and removals of syringes 200. In addition, the first and second legs 168, 170 of the flexing retaining member 166 are configured to provide tactile and/or audible feedback to a user upon correct installation and/or removal of the syringe 200.

In addition, the flexing retaining member 166 is provided with a pair of retention legs 175, 177 to prevent the syringe 200 from completely disengaging with the adapter 100 when a user presses on the syringe 200 through the third opening 119 to eject the syringe 200 from the syringe carrier section 106. The flexing retaining member 166 is also provided with a sloped surface 179 at an end of the flexing retaining member 166 that is positioned facing the cover portion 146. The sloped surface 179 extends towards the bottom of the syringe carrier section 106 of the adapter 100 and is configured to engage the flange 208 of the syringe 200 to allow for a more controlled pivoting action of the syringe 200 when a user presses on the syringe 200 through the third opening 119 to eject the syringe 200 from the syringe carrier section 106.

Figure 11:
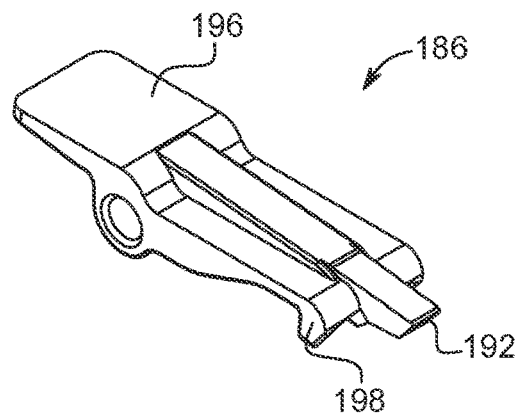
FIG. 11 is a perspective view of an engagement leg of an engagement mechanism of the adapter of FIG. 2 for connecting the adapter to a drive member of the injector system in accordance with the present disclosure.
Figure 12:
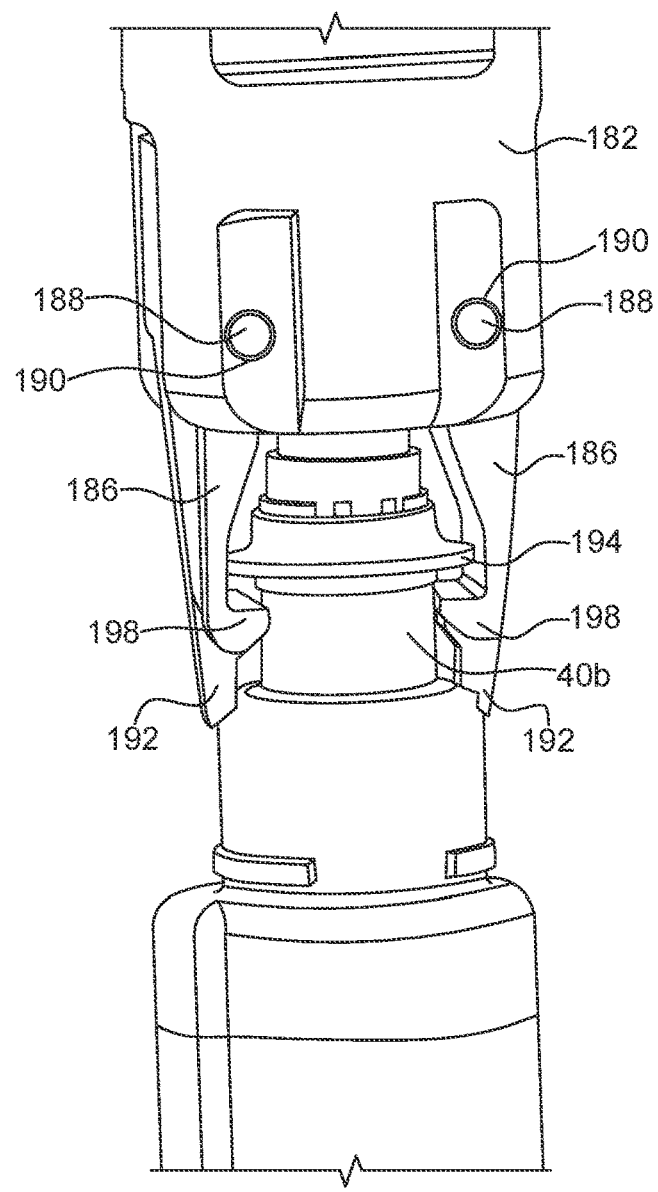
FIG. 12 is a perspective view of a pair of engagement legs of the engagement mechanism of the adapter of FIG. 2 connecting the adapter to the drive member of the injector system in accordance with the present disclosure.

With reference to FIGS. 11 and 12 and with continued reference to FIG. 3, as mentioned hereinabove, the push rod 52 includes an engagement mechanism 140 provided on the second end 138 thereof. The engagement mechanism 140 comprises an engagement hub 182, which is connected to the second end 138 of the push rod 52 via a dowel pin 184 or any other suitable attachment mechanism, and a pair of biased engagement legs 186 operatively connected to the engagement hub 182 via dowel pins 188 or any other suitable attachment mechanism. Each of the engagement legs 186 comprise a free first end 192 and a second end 196 that is connected to the engagement hub 182 via the dowel pins 188. In addition, the engagement legs 186 are biased by a spring element 190. The spring element 190 allows the engagement legs 186 to extend away from each other when the first end 192 of the legs 186 contacts a flange 194 of the drive member 40b of the injector 10 and then return to an engagement position when the first end 192 passes the flange 194 (see FIG. 12). The free first end 192 of each of the engagement legs 186 comprises a gripping member 198 configured to engage the flange 194 provided on the drive member 40b of the injector 10. The engagement mechanism 140 described hereinabove allows for installation of the adapter 100 in a non-orientation specific manner. This allows the adapter 100 to be connected to the injector 10 when the injector 10 is parallel to the ground. In this manner, the syringe 200 can be mounted within the adapter 100 with the adapter 100 being positioned parallel to the ground, thereby allowing the syringe 200 to be installed within the adapter 100 with less risk of the syringe 200 falling out during installation. While one example of an engagement mechanism is described hereinabove, this is not to be construed as limiting the present disclosure as any suitable engagement mechanism may be utilized to connect the push rod 52 to the drive member 40b of the injector, such as the engagement mechanisms disclosed in U.S. Pat. Nos. 6,984,222, and 7,419,478 and International Patent Application Publication No. WO 2015/142995, which are each hereby incorporated by reference.

In operation of the adapter 100, the push rod 52 makes a connection with the drive member 40b of the injector 10 as described hereinabove after the mounting mechanism 102 is attached to the front wall 80 of the injector 10. The syringe 200 can be top loaded via first opening 116 into syringe carrier section 106 either before or after connection of adapter 100 to the injector 10 via the mounting mechanism 102. The push rod 52 is advanced forward through the intermediate section 108 by the drive member 40b until the element 142 at the first end thereof pilots into the syringe plunger 54 to abut a rearward facing wall section within plunger 54. In one example, the element 142 is generally the shape of the rearward facing interior of the plunger 54. In this manner, the element 142 provides support to the plunger 54 to maintain the shape of the plunger 54 during use of the syringe 200. In many examples, the plunger 54 is fabricated predominantly from an elastomeric material. If the side walls of plunger 54 do not make adequate sealing contact with the interior side wall of syringe body 202, leakage of contrast to the rear of the plunger 54 can occur during advancement of the plunger 54. Thereafter, the contents of the syringe 200 are injected into a patient using the injector 10.

With returning reference to FIG. 1, the injector system 5 may be provided with a controller 300, such as a microprocessor, operatively connected to the injector 10, a display 302 operatively connected to the controller 300, and a user input device 304 operatively connected to the controller 300. The controller 300, display 302, and user input device 304 may be positioned adjacent to the injector system 5 and/or positioned remotely from the injector system 5, such as in a control room. The controller 300 may communicate with the injector system 5 via a wired or wireless connection. In addition, the display 302 may be configured as any suitable display for providing visual and/or audible information regarding the injection system 5 to a user. The user input device 304 may be configured as any suitable device for allowing a user to provide information to the controller 300. In one example, the display 302 and user input device 304 are integrated into a single device as a touch screen display.

The controller 300 is configured to receive user input and input from various sensors provided within the injector system 5 to control an injection procedure. With regard to the adapter 100 described herein, the controller 300 may be configured to receive information from the adapter 100 and adjust an injection procedure based on such information. For example, the adapter 100 may be configured to include an encoding device (not shown) positioned thereon and the injector system 5 may include a device operatively connected to the controller 300 for reading the encoding device. The encoding device may be a bar code having spaced bars, raised surfaces representing spaced bars, mechanically readable devices, e.g. a slot, hole, or projection on the mounting mechanism 102 designed to register against a switch on the injector 10, optically readable devices, e.g. characters, dots and other geometric shapes, that will send information concerning the adapter 100 to the controller 300, or a radio frequency identification device (RFID) tag. In one example, a base portion of the adapter which is inserted in the syringe port may include a pattern of grooves and ridges which can be identified by a scanner or sensor positioned in the injector syringe port as described in U.S. Pat. No. 7,018,363, the disclosure of which is incorporated herein by reference. Information captured by the sensor or scanner can be processed to identified the adapter type. Examples of the information which could be encoded on the encoding device include size of the adapter 100, types of syringes 200 that are compatible with the adapter 100, manufacturing information such as lot numbers, dates and tool cavity number, recommended contrast media flow rates and pressures, and loading/injection sequences.

In one example, the information from the encoding device of the adapter 100 is provided to the controller 300 when the adapter is mounted on the injector 10. Using this information, the controller 300 provides feedback to a user on the display 302 regarding the type of adapter 100 that has been installed. In some examples, based upon the adapter 100 that has been installed, the controller 300 could also display types of prefilled syringes that are compatible with the installed adapter 100. Alternatively, the injector system 5 is configured to allow a user to input a type of prefilled syringe using the user input device 304 that is used for an injection procedure. Based on this information, the controller 300 is configured to display on the display 302 the type of adapter 100 that is compatible with the selected syringe. In yet another example, the injector system 5 may be provided with a bar code or RFID reader (not shown) to read a bar code or RFID tag provided on the syringe 200. Based on the information from the bar code or RFID tag, the controller 300 is configured to display on the display 302 the type of adapter 100 that is compatible with the selected syringe.

Following an injection procedure, the controller 300 can be configured to automatically retract the drive member 40 and in turn the push rod 52 if, for example, the controller 300 receives a signal indicating that less than 5 mL of volume is remaining in the prefilled syringe 200 at the end of an injection procedure and/or if a user indicates the injection is completed by selecting, for example, an End of Case or Next Patient input on the user input device 304. Alternatively, the controller 300 may provide a popup display or message asking the user to confirm that the drive member 40 and push rod 52 should be retracted. This automatic retraction of the drive member 40 and the push rod 52 allows for removal of the prefilled syringe 200 from the adapter 100. In addition, prior to installation of a syringe 200 into adapter 100, if the push rod 52 is not positioned at or near the end of front face 150 of cover portion 146, the controller 300, based on input from a user through user input device 304, will be configured to automatically return the push rod 52 to a position at or near the end of front face 150 of cover portion 146 to allow for easy insertion of a new syringe 200.

Accordingly, the control and feedback systems of the present disclosure provide guidance to users in selecting and installing prefilled syringe adapters for powered injectors. A prefilled syringe adapter (PFA) can be selected based on the size and type of prefilled syringe being used for an injection. The control and feedback systems described herein can also determine parameter translation or calibration constants and limits for injection parameters based on the type of recommended or compatible adapter. For example, depending upon the diameter of the syringe, the parameter of milliliters injected per millimeter of travel will be different. Similarly, pressure per pounds of force on the push rod will differ and thus require translation in the control system. Different syringes may also have differences in the maximum pressure or pressure limit that is allowed.

Figure 13:
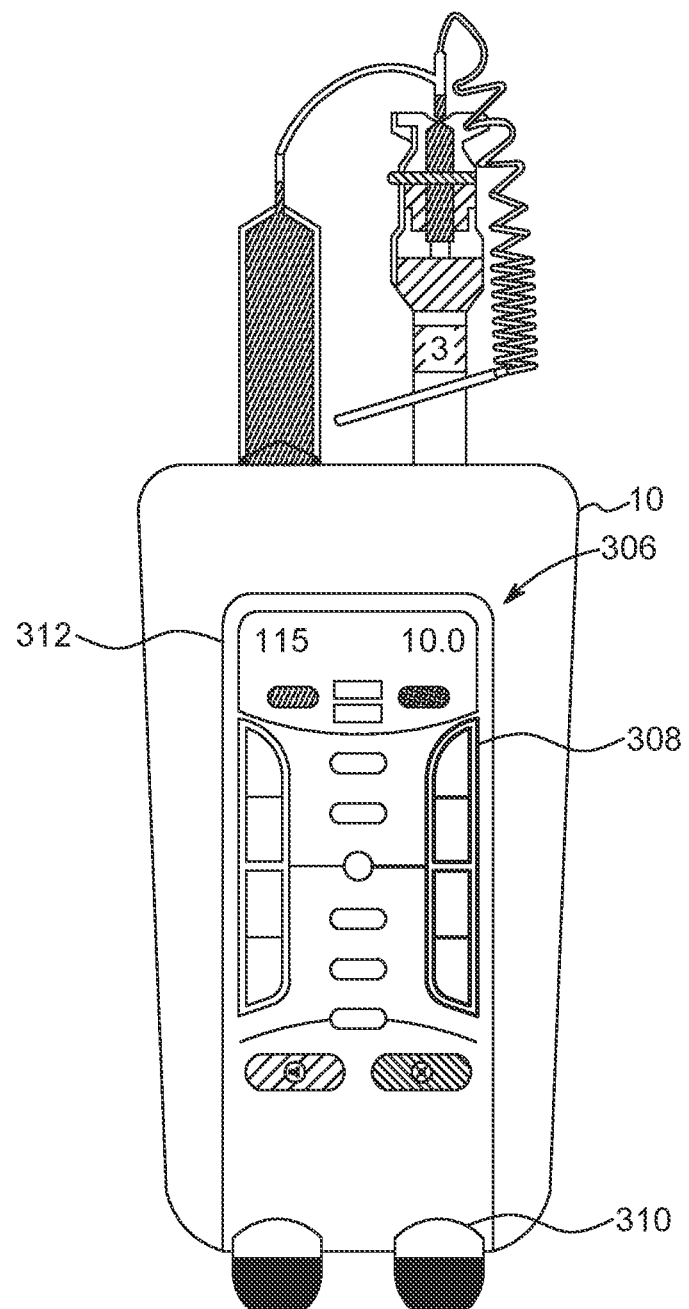
FIG. 13 is a schematic drawing of an injector in accordance with the present disclosure.

More specific examples of such control and feedback systems are provided with reference to the schematic drawing of the injector 10 provided in FIG. 13. As shown in FIG. 13, the injector 10 includes a front panel display 306 comprising a plurality of buttons 308 and knobs 310 for controlling the injector 10. For example, buttons 308 can be pressed to manually advance or retract the injector piston (e.g., by pressing and holding one of the buttons 308), as well as to initiate processes such as auto-priming saline solution or automatically retracting the injector and/or PFA piston after an injection has been completed. For example, a user may press a button 308 or twist a knob 310 to manually advance or retract the injector piston and adapter push rod. The front panel display can include a visual display 312, such as an LED display, showing numerical values for injection parameters or injection status information. In some examples, the injection parameter values can be determined based on which adapter is connected to the injector 10 or on the type of fluid to be injected. As described herein, the numerical values can also include an estimated volume of fluid remaining in a prefilled syringe connected to the injector calculated based on a position of the injector piston, push rod, and syringe plunger. The visual display 312 can also be used to instruct the user in preparing for an injection. For example, information, such as a recommended or compatible adapter type, can flash on the display 312 to inform the user of the recommendation. The injection parameters can also be displayed on screens of a user interface on the display 302 of the injector system 5.

The injector system 5 can include a graphical user interface configured to be displayed on the display 302 for guiding a user through initial injector setup, injection preparation, performing the injection, and post-injection processes. The user interface can include a number of different screens and popup boxes or menus for providing information to the user about a process being performed and for receiving input from the user about the patient, syringe, adapter, and other system components. The user interface can be displayed on a touchscreen device, such as a computer tablet or laptop. In that case, the user can interact with the user interface by touching different portions of the display screen to record selections. In other examples, the display 302 can be a conventional computer with input accessories including a mouse and keyboard. In that case, the user can input selections and information by using the mouse to click on a portion of the display screen or by typing information using the keyboard in a conventional manner.

Figure 14:
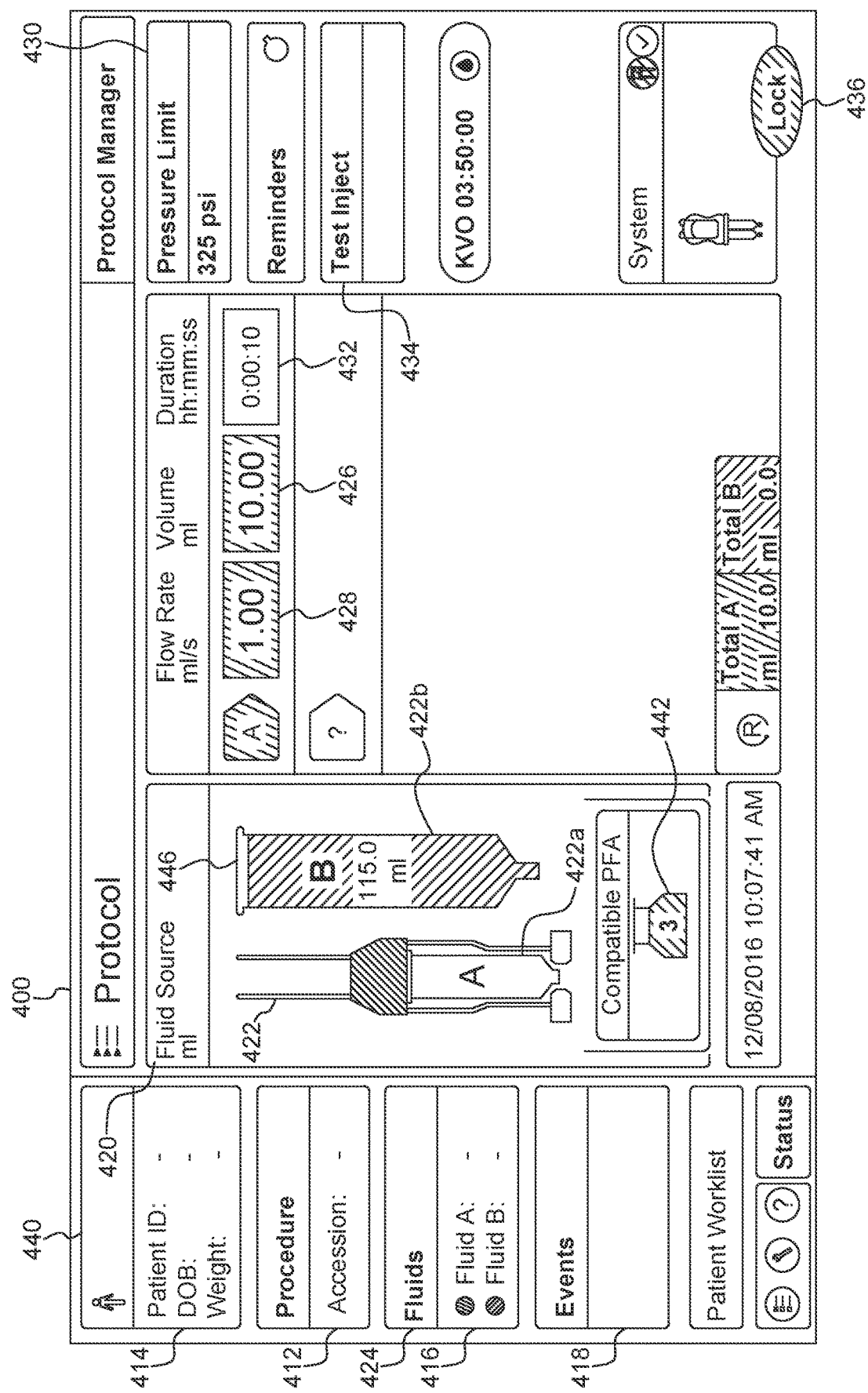
FIG. 14 is a schematic drawing of a user interface screen which can be displayed on a display of an injector system for controlling and providing feedback about an injection procedure performed using the system in accordance with the present disclosure.

In most cases, the user will first be presented with an overview or protocol screen including information about the patient and procedure to be performed. An exemplary protocol screen that can be shown on display 302 is depicted in FIG. 14. The screen 400 includes a portion 412 identifying the injection procedure to be performed, a patient information portion 414, a fluids portion 416 displaying types of fluids contained in syringes mounted to the injector, an events portion 418, and a central portion 420 with information about the injection protocol to be performed. In some examples, the screen 400 can also include a message portion (not shown), which permits a user to send and receive messages from individuals at other locations. For example, a system operator may send a message to a technician standing near the injector. Messages may be required, for example, if the display 302 is located in a control room remote from the injector, meaning that the system operator and technician cannot talk to one another.

The screen 400 can also include a plurality of virtual buttons which can be selected by the user to input information about an injection procedure and/or to control operation of the injector. For example, pressing a radio button 424 associated with the fluids portion 416 of the screen 400 may generate a popup box with additional information about fluids contained in the syringes. Pressing the button 424 may also cause either a fluid delivery set up screen (shown in FIG. 18A) and/or a contrast setup screen (shown in FIG. 18B) for manually selecting which fluids will be injected. Other virtual buttons allow a user to access a protocol manager and to schedule events or reminders. Still other virtual buttons can be used to control the injector. For example, the screen 400 can include a test inject button 434 to activate the injector and/or a lock button 436 which locks the injection protocol and allows the user to arm the system. In some examples, the screen 400 can also include buttons for manually or automatically advancing the injector piston to prime the fluid path or to retract the injector piston following an injection so that an empty syringe can be removed from the adapter or syringe port.

In some examples, the patient information portion 414 of the screen 400 displays fields including a patient ID number, date of birth, weight, and other patient characteristics. The patient information can be manually entered or can be automatically populated from information stored on system memory associated with the injector system or downloaded from an external database, such as a medical facility patient electronic health record database. In order to manually enter information, the user interface can display a virtual keyboard on the screen allowing the user to type information, such as the patient name and physical characteristics. Information may also be typed or selected using an input accessory (e.g., a keyboard or computer mouse) associated with the display 302 (shown in FIG. 1). In some examples, information fields can be populated based on a selection entered by the user. For example, the user interface can allow a user to select a patient for an injection to be performed from a list of previous patients. Once the patient is selected from the list, information such as name, date of birth, and other fields can be automatically populated from information stored on system memory associated with the injector system.

Figure 16:
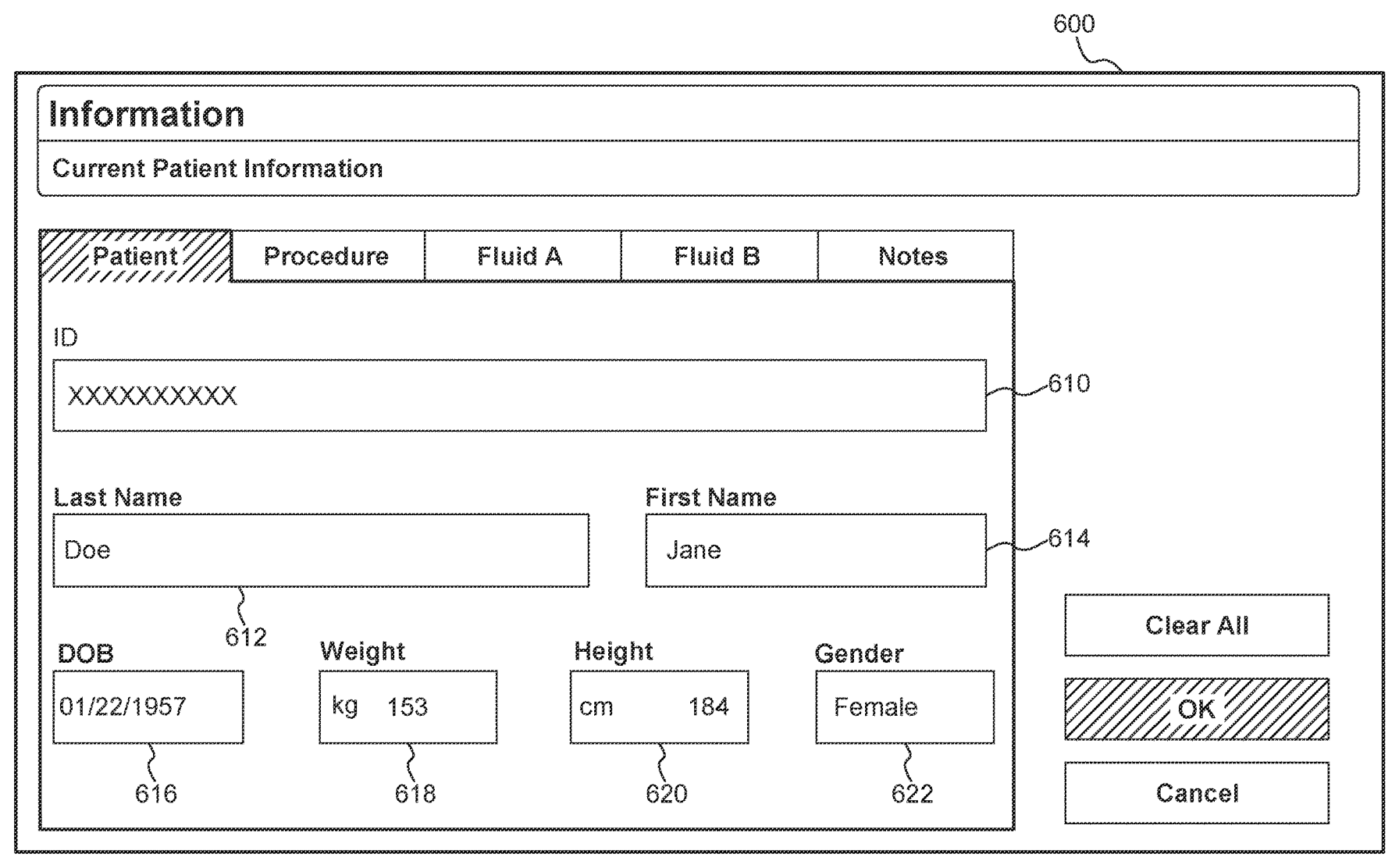

The patient information portion 414 also includes a button 440 which can be selected by the user to display a popup box with additional patient information. When the button 440 is pressed, a screen or popup box 600 (shown in FIG. 16) with a patient information tab is displayed to the user. The screen 600 includes fields for information such as a patient ID number 610, last name 612, first name 614, date of birth 616, weight 618, height 620, and gender 622. The information can be more detailed than information shown on the protocol screen 400. In some examples, a user can either scan a patient's identifying tag, such as on an informational bracelet, or manually update information in the patient information fields by, for example, selecting a field and typing in new data. In some examples, fields can be automatically populated. For example, a user can manually enter a patient name or ID number for a new patient. The system can also search a patient database for the name or ID number and populate remaining patient fields based on information in the database.

In some examples, the fluids portion 416 of the display screen can list fluids contained in a syringe connected to syringe ports A and B. As described above, to review additional information about fluids being injected, a user can select the button 424 to generate a screen or popup box including additional information about the current syringes.

Figure 17:
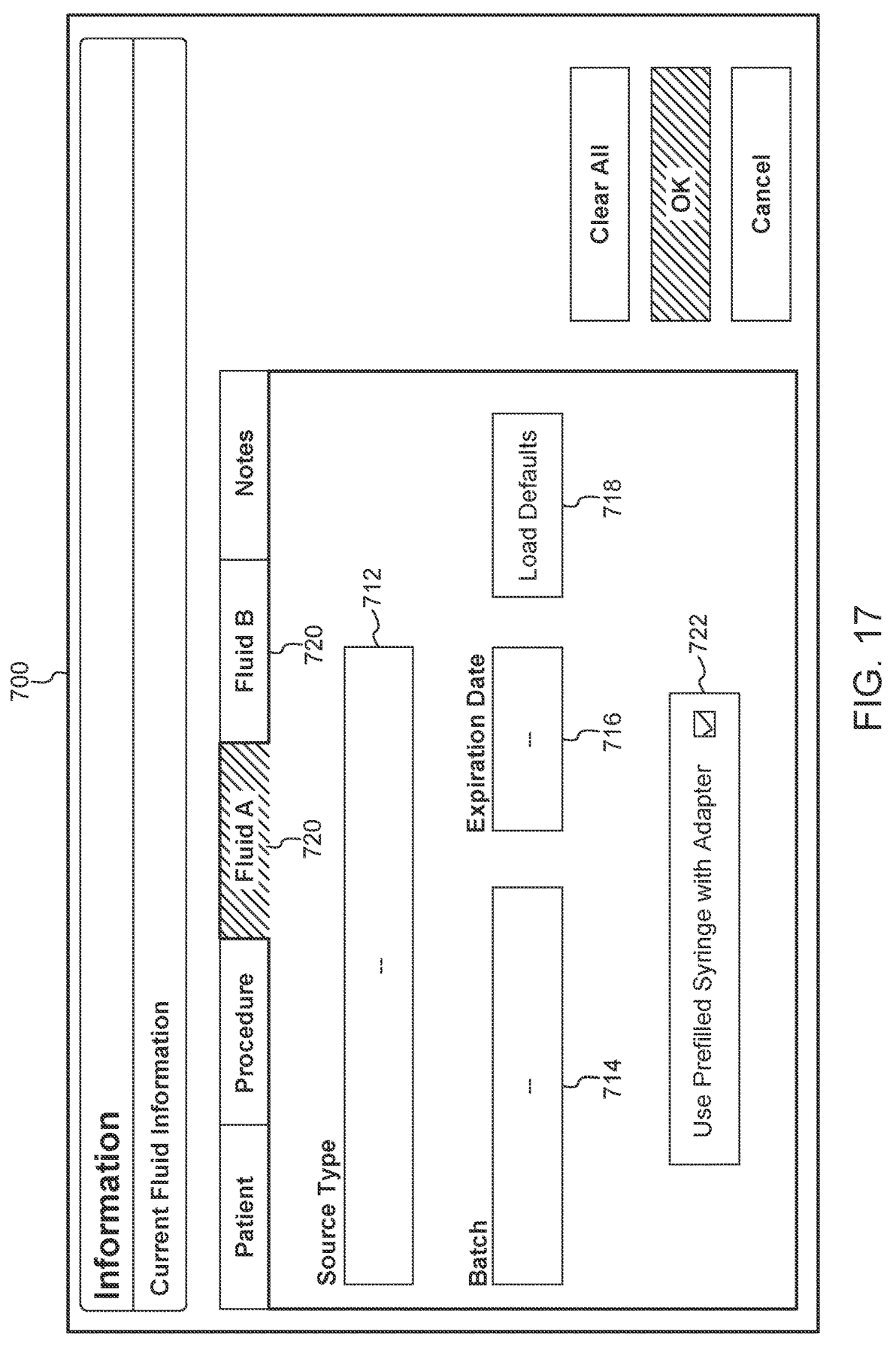

An exemplary current fluid information screen or box 700 is shown in FIG. 17. The screen or popup box 700 includes fields for a type of contrast or source type 712 (e.g., identified by tradename and manufacturer), batch number 714, and expiration date 716. This information is traditionally printed on a label of a prefilled syringe. In some examples, a user can manually enter information from the syringe label into the injector system using the user interface. In other examples, information can be electronically scanned from a syringe label or bar code. In other examples, the information can be stored in an inventory database. When the user selects the fluid name, other information about the fluid and syringe can be downloaded from the database and shown in the popup box 700. In some examples, the screen 700 can include a virtual button or check box (not shown) allowing a user to select whether the fluid should be delivered using an adapter. When the box is selected or checked, the system can provide a recommendation for what type of adapter to use for delivering the identified fluid. In some examples, a user can select default fluid types by selecting the "Load Defaults" button 718 in FIG. 17. As shown in FIG. 17, a user can switch between reviewing information for the fluid in syringe A and the fluid in syringe B using a series of tabs 720 located near the top of the box 700. The box 700 also includes a check box 722 allowing the user to select whether the injection will be performed with a prefilled syringe adapter. When the check box 722 is selected, the system provides feedback about a compatible or recommended PFA, for use with the selected contrast fluid and other injection parameters. For example, as discussed in connection with FIG. 14, a PFA icon could be displayed showing the user the compatible or recommended PFA.

With reference again to FIG. 14, the central or protocol portion 420 of the screen 400 includes detailed information about injection parameters for an injection to be performed. In some examples, the protocol portion 420 comprises visual indicators or icons 422 depicting syringes and/or adapters. For example, an icon 422b depicting a syringe is labeled "B" indicating that it depicts a syringe mounted to syringe port B of the injector. Since the icon 422b does not show an adapter, it is understood that the syringe mounted in syringe port B is a native syringe sized to be directly mounted to syringe port B. In some examples, such a native syringe contains saline solution configured to be mixed with a contrast agent prior to delivery to the patient. An icon 422a of a syringe and adapter labeled "A" is also shown in the protocol portion 420. Since both the syringe and adapter are shown, the icon 422a indicates that the syringe will be connected to the syringe port A with an adapter. The icon 422a shown in FIG. 14 does not identify the adapter type. For example, the icon 422a does not include a number or color which would inform the user what adapter type to use. As such, the icon 422a may indicate that an adapter is needed for the injection, but has not yet been inserted in syringe port A. For example, the icon 422a could include a dashed outline of an adapter indicating that an adapter is needed but not yet installed. In that case, the protocol portion 420 of the screen 400 can also include a recommended or compatible adapter icon 442 indicating a type of adapter which can be used for an injection procedure to be performed with the selected contrast fluid. For example, the icon 422a can be a particular color or number corresponding to a specific adapter size or configuration. In some cases, the injector is capable of receiving a number of different adapter types. In some examples, each adapter type can be assigned a number (e.g., 1-5) and/or color (e.g., red, green, yellow, blue, purple). The compatible adapter icon 442 can include an image of the recommended or compatible adapter along with a visual representation of the recommended adapter's assigned number and/or color. For example, compatible adapter icon 442 in FIG. 14 indicates that adapter type "3" should be inserted into syringe port A. In some examples, the icon 442 may also indicate when an incompatible PFA is installed. For example, the icon 422 could include an "x" or cross over the visual representation of the PFA showing a user that the installed PFA is incorrect.

In some examples, once an adapter is installed in syringe port A of the injector, the icon 422a may change shape to depict that the adapter has been installed. For example, once the adapter is installed in the syringe port A, the icon 422a can be updated to, for example, replace dashed lines with solid lines or to show the number and/or color of the installed adapter. In some examples, the icons 422 are animated icons which change appearance as an injection is being performed to indicate status or progress of the injection. For example, the icons 422 can depict whether the prefilled syringes mounted to the injector are empty, full, or to show an amount of fluid remaining in the syringe. As an injection is being performed, fluid volume shown by the icons 422 decreases. For example, in FIG. 14, icon 422b is shown filled with fluid F. As an injection is being performed, fluid level line 446 in the syringe can decrease indicating that fluid is being expelled from the syringe connected to syringe port B. Following completion of the injection procedure, the icons 422 may show that the syringe(s) are empty to indicate that all fluid contained in the syringe(s) has been delivered to the patient. In addition, a message or animation can be displayed on the screen 400 to indicate that the injection has been completed. In a similar manner, a message can be displayed asking the user whether the piston should be retracted. Once the piston rod is fully retracted, a message can be displayed indicating that the user can remove the used syringe from the adapter.

The protocol portion 420 of the screen 400 also includes numerical representations of different injection parameters. For example, the protocol portion 420 may show numerical values for injection volume 426, flow rate 428, default (maximum) pressure limit 430, and injection duration 432. In some examples, injection parameter information is manually entered. For example, as discussed in connection with entering patient information, a virtual keyboard may be displayed on the protocol screen 400. The keyboard can be used to manually enter injection parameters for the injection to be performed. In other examples, an input component or accessory can be used for manually entering information about an injection to be performed. In some examples, injection parameter information is determined based on the type of adapter installed on the injector and/or on the type of fluid or prefilled syringe being used for the injection. In other cases, information about the type of adapter or prefilled syringe may be used to establish maximum values or ranges of acceptable values for different injection parameters. In that case, a user may be able to select injection parameters for the injection using the fluid delivery setup screen shown in FIG. 18A. However, a warning may be provided if the parameters selected by the user are outside of an acceptable range for the adapter being used.

Figure 15:
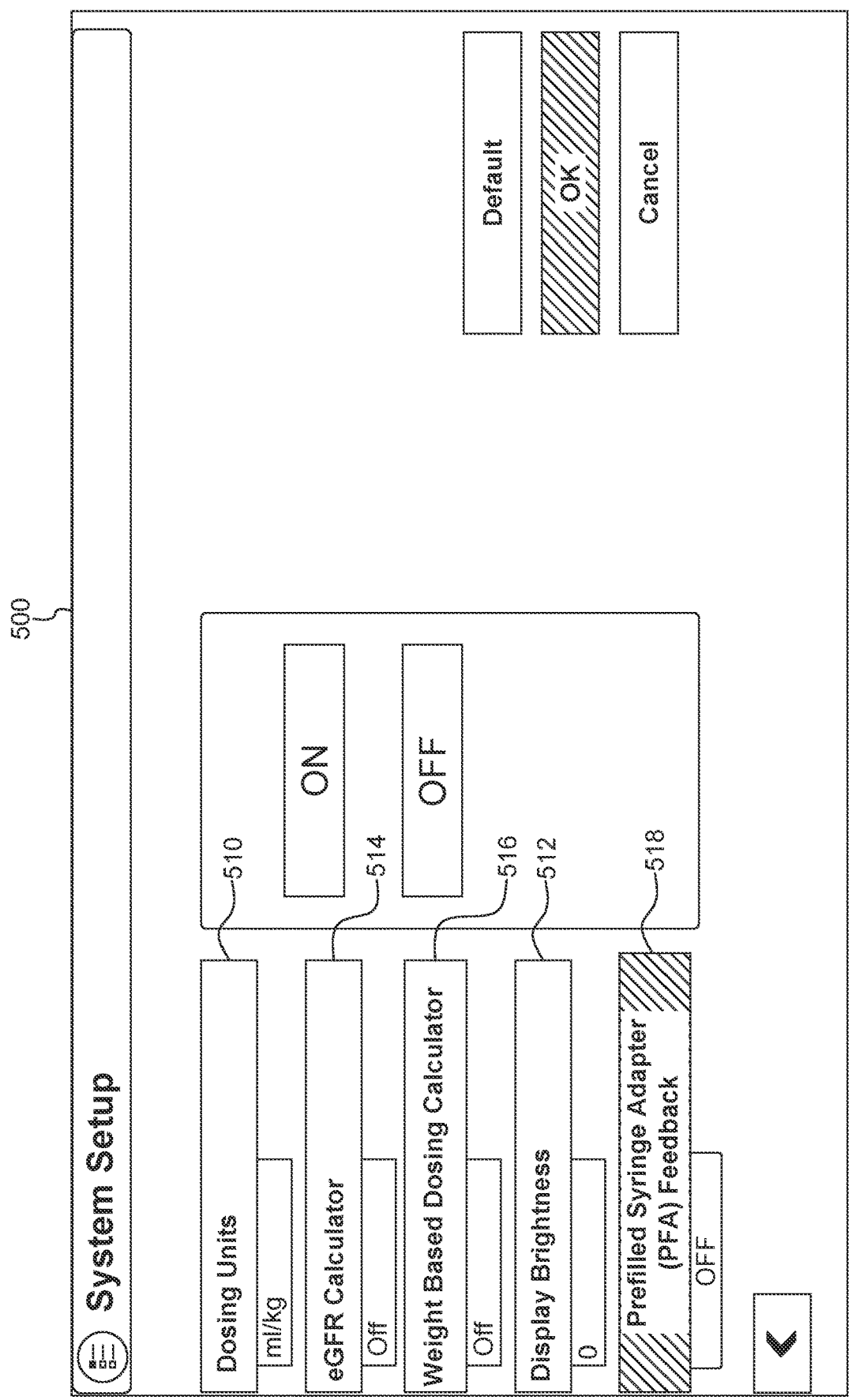
FIG. 15 is a schematic drawing of another user interface screen for an injector system in accordance with the present disclosure.

With reference to FIG. 15, a system setup screen 500 accessible from the protocol screen 400 is shown. For example, a user may select or press a button on the protocol screen to open the system setup screen 500. The setup screen 500 is typically opened the first time that a user uses the system to select his or her preferences. The setup screen 500 allows the user to make selections about appearance of user interface screens and to turn on or off different user interface features. Default preferences can be saved and loaded each time that the user uses the system. For example, a user can select which units doses are displayed in using the button 510 or may set levels for screen brightness 512. The user can also turn certain user interface features on and off from the screen 500. For example, a user can decide whether to turn on or off features including an estimated Glomerular Filtration Rate (eGFR) calculator 514 or weight based dosing calculator 516. The user can also decide whether to turn the PFA Feedback 518 feature on or off. The feedback feature provides the user with information about what PFA adapter should be used for particular procedures. The feedback can also confirm whether a PFA installed on the injector is incorrect for a procedure to be performed. In some cases, feedback can inform the user that none of the available adapters are approved for use with the syringe or fluid to be injected during a particular procedure. In that case, the user may need to select a different type of fluid or a different type of prefilled syringe for an injection procedure.

Figure 18A:
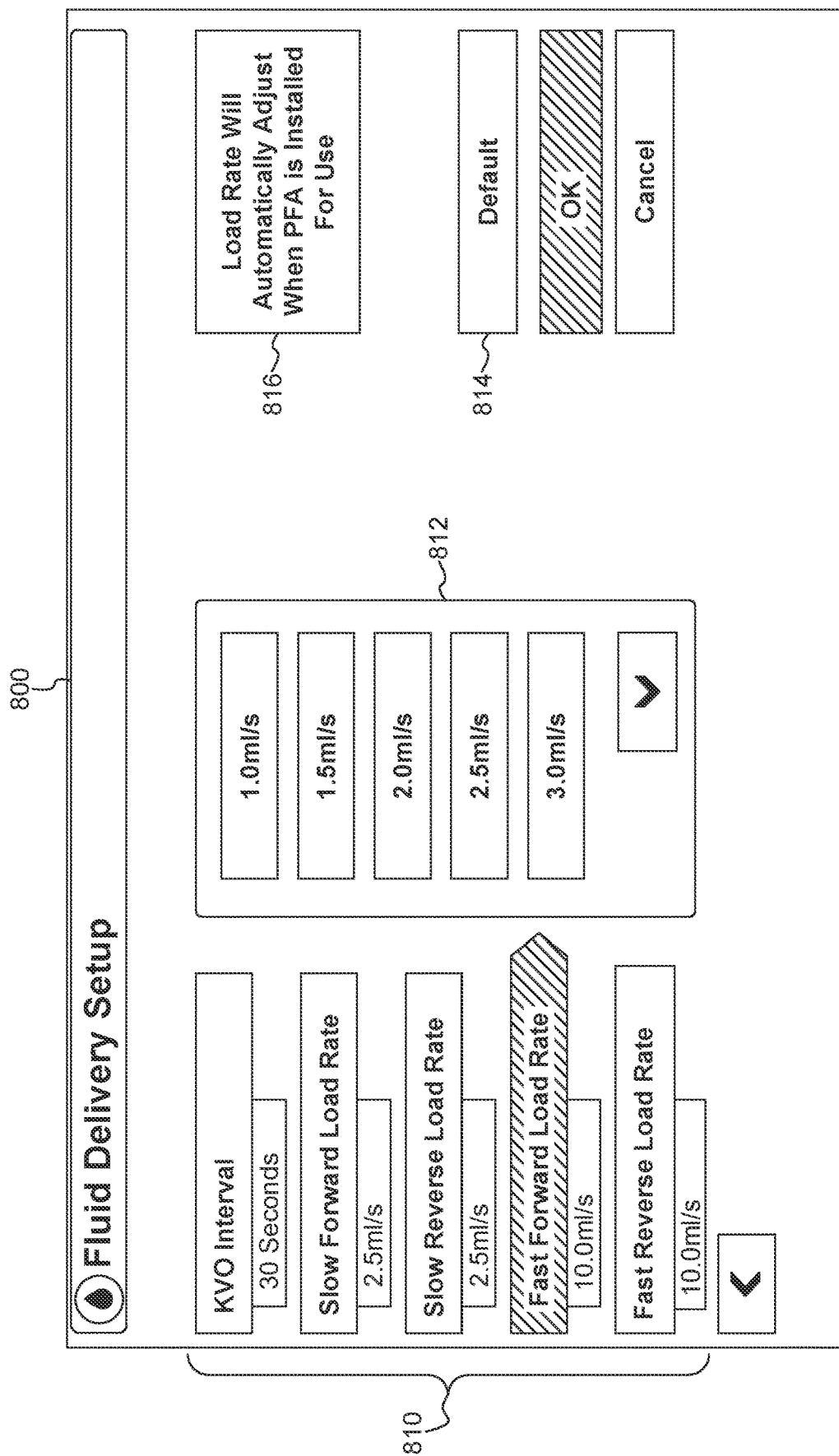

With reference to FIG. 18A, the fluid delivery setup screen 800, which can be accessed from the protocol screen 400, is illustrated. The fluid delivery setup screen 800 includes a list 810 of injection parameters. These parameters may be adjusted prior to each injection procedure or may remain the same for a series of procedures. The listed parameters can include a keep vein open (KVO) interval, slow forward load rate, slow reverse load rate, fast forward load rate, and fast reverse load rate. In order to select a numerical value for a parameter, a user presses a virtual button associated with a parameter of interest, which displays a list 812 of options. For example, as shown in FIG. 18A, selecting "fast forward load rate" displays a list of values from 1.0 ml/s to 3.0 ml/s. The screen 800 can also include a virtual button 814 allowing a user to select preloaded default values for the injection parameters. The user's selections can be saved by the system until an injection is ready to be performed. In addition, as shown in FIG. 18A, the screen 800 can include a message box 816 confirming that the selections have been received and stating that "Load Rate will Automatically Adjust when PFA is Installed for Use".

As shown in FIG. 18B, a similar menu screen, referred to as a "Contrast Type" screen 820, can be used to enter information about different contrast fluids into the system or to identify the contrast or fluid type to be delivered to the patient in an injection procedure. Using the screen 820, the user can select the type of contrast to be delivered along with parameters including concentration and vial size. In some examples, the user can also enter dosage information 822, dosage weight limits 824, dosage minimum age 826, and other characteristics for different contrasts, which can be used to confirm that the selected contrast is appropriate for the patient and injection protocol. When contrast name button 828 is selected, a list 830 of contrast fluids which can be delivered to the patient is displayed. As shown in FIG. 18B, the list 830 includes Gadovist®, Magnevist®, Primovist®, Prohance®, Magnescope®, and Multihance®. Other contrast fluids including Dotarem® can also be used with the system disclosed herein as each are readily commercially available. Once the user selects the type of contrast for the injection, a popup box 832 can be displayed asking the user to confirm the type of contrast selected or, for example, to confirm information about the selected contrast fluid, such as the name of the manufacturer or seller of the selected contrast fluid. These questions can be a confirmation that the user has selected the correct fluid for the procedure to be performed. For example, the popup box 832 in FIG. 18B asks the user to confirm that the selected contrast fluid to be used for a procedure was sold by Eisai. Information about contrast fluid manufacturer or seller can be entered and saved along with other information about contrast fluid during an initial setup or contrast configuration process for the system. In some examples, the contrast setup screen in FIG. 17 can be used for entering information about particular contrast fluids. Following initial contrast setup, the user can edit or update the contrast and manufacturer information while using the system by selecting a Contrast Edit screen from the user interface. In some examples, the system can also provide feedback based on a type of contrast selected by the user. For example, when the user selects a type of contrast and vial size which is compatible with a PFA, the compatible PFA icon can be displayed on the screen to inform the user that fluids being prepared for use are compatible with certain PFA devices.

The injector system and user interface described herein can be used to guide the user through performance of a number of different injection procedures and cases. For example, the user interface screens can assist a user in preparing the injector and syringes, operating the injector, and, following the injection, preparing for another injection for the same or a different patient. Feedback provided through the user interface can address a number of different use cases including, for example, when an incorrect adapter is installed or when a selected syringe or fluid-type is not compatible with any available adapters. Exemplary injector preparation and fluid delivery processes are shown in FIGS. 19-22.

Example 1: Standard Fluid Delivery Procedure

Figure 19:
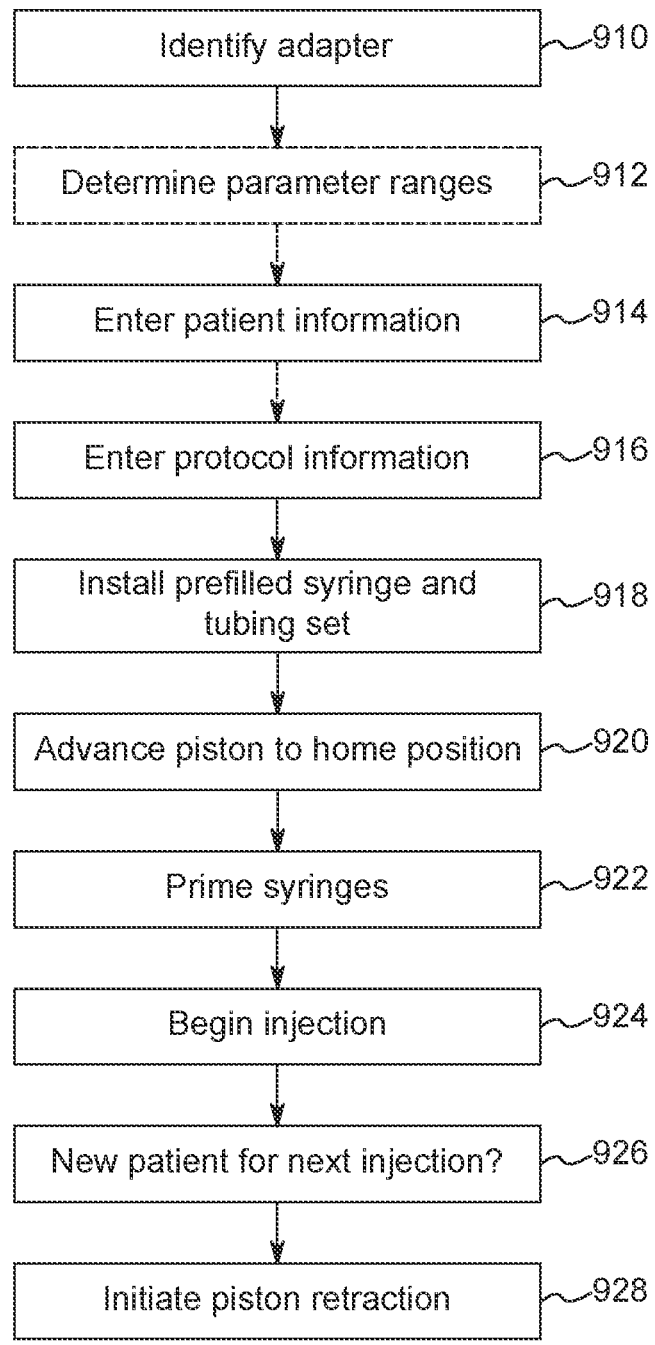
FIG. 19 is a flow chart showing a process for preparing and performing an injection with an injector system in accordance with the present disclosure.

As shown in FIG. 19, a flow chart of a process for performing a fluid delivery procedure with the injector system and for displaying information about the injection with the user interface is illustrated. In this example, the adapter is initially connected to the injector. For example, the adapter may have been used in a previous injection procedure and is still connected to the injector. Alternatively, the user may know which adapter to use with a particular prefilled syringe and install the adapter to the injector before performing other injection preparation activities.

As shown at 910, the system is configured to identify the installed adapter. For example, information about the type of adapter can be automatically extracted from a bar code or design on the adapter itself. In one example, a base portion of the adapter which is inserted in the syringe port may include a pattern of grooves and ridges which can be identified by a scanner or sensor positioned in the injector syringe port. Information captured by the sensor or scanner can be processed to identified the adapter type. Optionally, maximum acceptable injection parameter values or acceptable ranges for injection parameters can be determined from system memory, as shown at 912, based on the identified adapter type. Injection parameters that can be determined based on the identified adapter type can include maximum syringe volume, flow rate, default (maximum) pressure limit, and forward/reverse piston control speeds based on the identified adapter.

As shown at 914, a user may enter patient information for the injection to be performed using the user interface. Patient information can include a patient ID number, name, date of birth, weight, and height. As described herein, patient information can be entered manually or scanned from a patient identifying tag, such as a bracelet. In other examples, a user may select a patient's name from a list of previous patients or query and search a patient database. In that case, patient information for the selected patient can be obtained from system memory or hospital records. As shown at 916, the user may then enter protocol information for the procedure to be performed. For example, the user may enter fluid information using a portion of the user interface screen shown in FIG. 18B. Fluid information can include source type, batch number, expiration date, and other information, which is generally printed on a prefilled syringe label. The user may also enter injection parameters, such as fluid volume and rate using the fluid delivery setup screen shown in FIG. 18A. The entered fluid delivery or injection parameters can be displayed in the protocol portion 420 of the protocol screen 400. Once the injector and protocol information are determined or manually entered, as shown at 918, the user installs the prefilled syringe into the adapter and connects a tubing set for transporting fluid from the syringe to the patient.

After the prefilled syringe and tubing set are connected, as shown at 920, the injector piston is advanced through the syringe port from a home position towards a plunger of the prefilled syringe. Since the actual position of the plunger in the prefilled syringe is not known when the injector piston begins to advance past the home position, the system assumes or estimates that the syringe is filled with fluid. In that case, the LED display of the injector and protocol screen 400 of the user interface may display the syringe maximum estimated fluid volume. In addition, the syringe icon 422*a* on the protocol screen 400 can show that the syringe is filled with fluid. As the PFA piston advances through the adapter past the home position or past another selected position, such as a position corresponding to the syringe plunger position when the syringe is filled with fluid, the fluid volume displayed on the injector and protocol screen decreases. For example, the selected position could be a position 1 mL above the home position. In addition, the fluid level shown by the syringe icon 422*a* on the protocol screen 400 (shown in FIG. 14) moves downward towards the distal end of the syringe indicating decreased fluid volume.

Once injector pistons are connected to the plungers of the respective syringes, as shown at 922, a priming process can be performed. For syringes connected to a syringe port through the PFA, such as a syringe containing contrast fluid, the user performs a two-step priming process. First, the user manually advances the injector piston, such as by pressing and holding a button on the injector housing, to prime contrast fluid from the syringe barrel to a T-connector portion of fluid tubing. Once the contrast fluid is manually primed to the desired position, an automatic priming process can be performed to prime a saline syringe. For example, an auto-prime button may appear on the user interface screen for the user to select. During auto-priming, since the saline syringe is connected directly to the injector (such as saline syringe B), priming can be performed automatically since the position of the plunger and fluid volume contained in the syringe are known. During the auto-priming process, the piston is advanced a predetermined distance from its home position to expel saline from the saline syringe and into tubing connecting the syringes to other portions of the injector system. In some examples, the system may prevent the user from beginning the auto-priming process if a PFA piston for the contrast syringe (in syringe port A) is not at least slightly above its home position, since such positioning would indicate that the user has not manually primed the contrast fluid as required In some examples, the user interface can guide the user through the manual priming process to address any difficulties the user may have in priming the contrast syringe. For example, a message instructing the user to press and hold the injector piston advance button could be displayed on the user interface display. After the injector piston advances a distance based on how long the user holds the advance button, the user interface could display a message instructing the user to press the auto-prime button once the fluid level reaches the tubing set. In some instances, the auto-prime feature may be enabled only after the manual priming process has been sensed by the system to have been completed. In a similar manner, the user interface can be configured to prevent the user from arming and/or attempting to perform an injection until priming is completed. For example, if the user attempts to arm the injector system or perform an injection without first priming air from the system, the user interface may display a warning or alert informing the user that such actions cannot be performed without first priming the syringe(s) and tubing.

Once the tubing is primed, as shown at 924, the user can set the injector system to begin an injection. For example, the user can initiate a lock and/or arm protocol by pressing appropriate buttons displayed on the user interface. Once the injector is locked and armed, the injection is performed. For example, piston rods can be advanced through the syringe port and adapter causing the syringe plungers to advance through the syringes to expel fluid therefrom. The pistons continue to advance until a preselected injection volume has been delivered to the patient or until the syringes are empty. Once the desired fluid volume has been delivered to the patient, an injection complete message may be displayed on the injector and/or on the user interface confirming for the user that the desired amount of fluid has been delivered.

Following the injection, as shown at box 926, the system may ask the user to select whether the next injection will be for the same patient or for a new patient. The user may submit an answer with the user interface. Alternatively or in addition, as shown at box 928, the injector system can automatically or in response to a request by the user initiate an injector piston retraction process allowing a user to remove an empty syringe from the adapter. The injector piston retraction can be an auto-retract process in which the injector automatically withdraws the piston from the syringe plunger and back into the syringe port. For example, the piston can also be retracted back to its home position. Alternatively, the user may manually retract the piston by pressing and holding a piston retract button on the injector or user interface until the piston retracts to a desired position. Once the piston is retracted the user can remove the empty syringe from the injector device.

Example 2: Adapter not Initially Installed on Injector Unit

Figure 20:
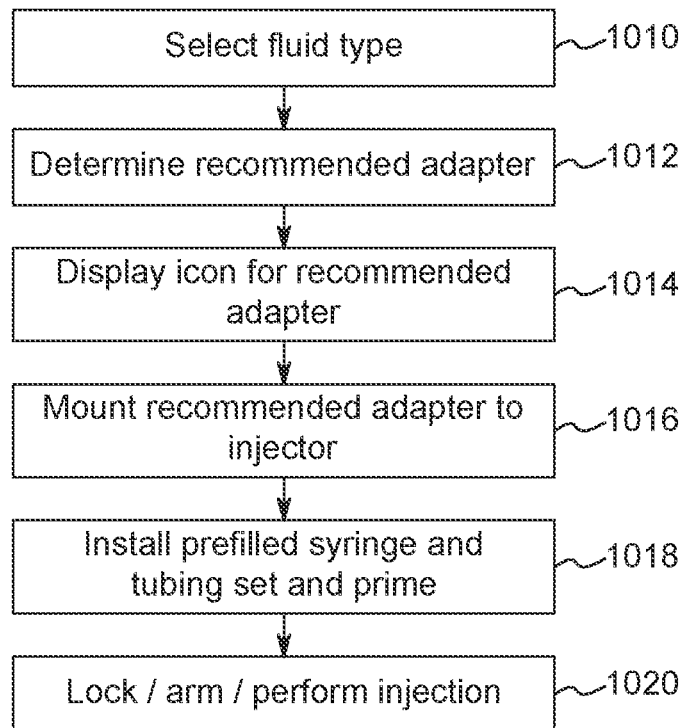
FIG. 20 is a flow chart showing another example process for performing an injection with the injector system in accordance with the present disclosure.

FIG. 20 depicts a flow chart for another example fluid delivery process using the injector and user interface is illustrated. In this example, the adapter is not initially installed on the injector. Instead, in the process of FIG. 20, the user interface provides a recommendation for an adapter to use based on information entered by the user.

As shown at 1010, the user selects a fluid type for the injection to be performed. For example, the user can enter a type of fluid, batch number, expiration date, and other information using the current fluid information screen described above. The user may also indicate that the fluid should be delivered using an adapter by, for example, checking a "Use Adapter" box on a current fluid information popup box or screen, as shown in FIG. 17. Once the current fluid information is entered, as shown at 1012, the injector system can determine a recommended or compatible adapter which can be used with the prefilled syringe and fluid to be delivered. As shown at 1014, an icon indicating the recommended adapter type can be displayed on one of the user interface screens. For example, an icon or image of the recommended or compatible adapter may be displayed on the protocol screen 400, shown in FIG. 14. A number for the recommended or compatible adapter (e.g., 1-5) can also be shown on the injector itself. For example, the number for the recommended adapter can flash or blink on the front panel display of the injector shown in FIG. 13. The number for the recommended adapter can continue to flash until a predetermined timeout period has expired, until a correct adapter is installed, or indefinitely. If an incorrect adapter is installed, the injector display may continue blinking to indicate to the user or technician that the adapter should be replaced. In a similar manner, as described herein, a message indicating that the wrong adapter has been installed could be displayed on the user interface.

As shown at 1016, the user installs the recommended or compatible adapter to the injector. The injector display stops blinking once the injector senses that the correct adapter has been installed as previously described. As shown at 1018, the user then installs the prefilled syringe and tubing and advances the injector piston past the home position, as described above in connection with FIG. 19, and continues with the priming task and entry of protocol information 916, if such a task has not been completed previously. As shown at 1020, the user then locks and arms the injector and performs the injection as described above.

Example 3: User Installs Wrong Adapter

Figure 21:
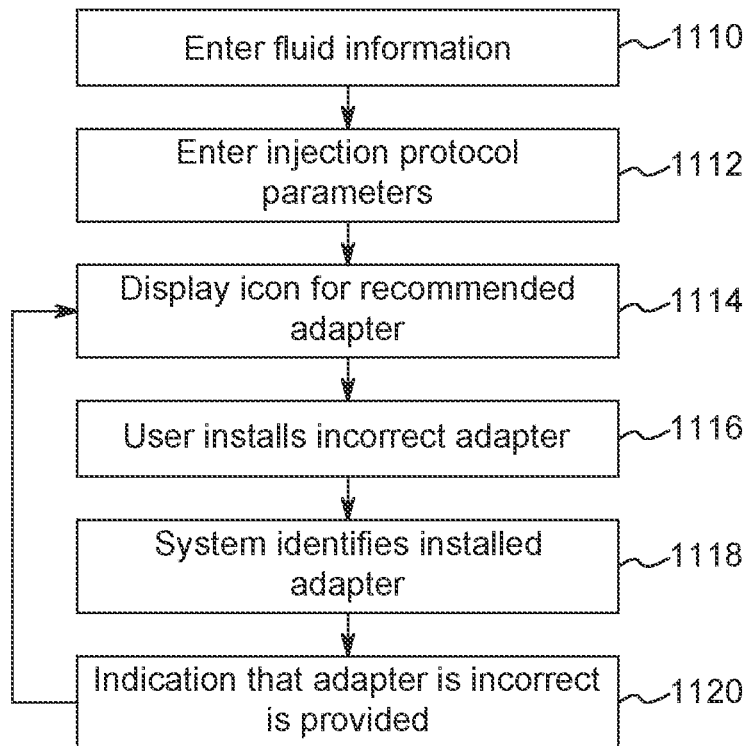
FIG. 21 is a flow chart showing another example process for performing an injection with the injector system in accordance with the present disclosure.

An example case in which a user installs the wrong adapter is shown in FIG. 21. As shown at 1110 and 1112, the user enters information for the fluid and protocol as described above. Once the fluid and protocol information is entered, as shown at 1114, a recommendation for an adapter to be used is determined by the system and the recommended or compatible adapter icon is displayed on the protocol screen of the user interface. At 1116, the user installs an adapter to the syringe port. However, the installed adapter is not a recommended adapter or an adapter which is compatible for the injection procedure to be performed. As shown at 1118, the injector system identifies the installed adapter and, as shown at 1120, generates a message that the adapter is incorrect or not compatible for a scheduled injection procedure. For example, a popup message can appear on the protocol screen of the user interface informing the user that an incorrect adapter has been installed. The user may be required to acknowledge the popup box by, for example, selecting an "OK" button on the popup box. After the message is acknowledged, the icon or message indicating the recommended size/type of syringe can be displayed again on the user interface. The user can review the recommendation and install another adapter or syringe. Alternatively, after acknowledging the popup message, the user could continue to perform the injection using the installed syringe and adapter. In particular, the system does not prevent the user from performing an injection if a detected adapter is identified as being incompatible with an injection to be performed. Instead, the user is permitted to continue performing the injection after the popup message is acknowledged.

The user interface can also identify that a selected fluid is not compatible with any of the available adapters. For example, the user may enter a fluid type in the current fluid information screen and check a "Use adapter" box indicating that an adapter should be used for the injection. However, if the fluid name entered by the user is not recognized and/or is not supported by the injector system, a warning may be displayed. For example, the warning may state that the entered fluid and prefilled syringe are not compatible with any of the adapters. The user may be requested to acknowledge the popup box by selecting an "OK" button. An icon indicating that none of the adapters are recommended for use with the fluid and syringe can also be displayed on the protocol screen.

If the user knows that the fluid and syringe can be used with one of the available adapters, the user can override the warning and install the adapter. The system can be configured to allow the user to continue with the injection once the adapter is installed. The injector system generally is not configured to prevent the user from performing an injection. Instead, the popup box is only meant to be a notification asking the user to reconsider or confirm that the syringe and fluid are correct. The adapter feedback and user interface is not meant to prevent the user from controlling the injection.

Example 4: Automatic Syringe Identification

Figure 22:
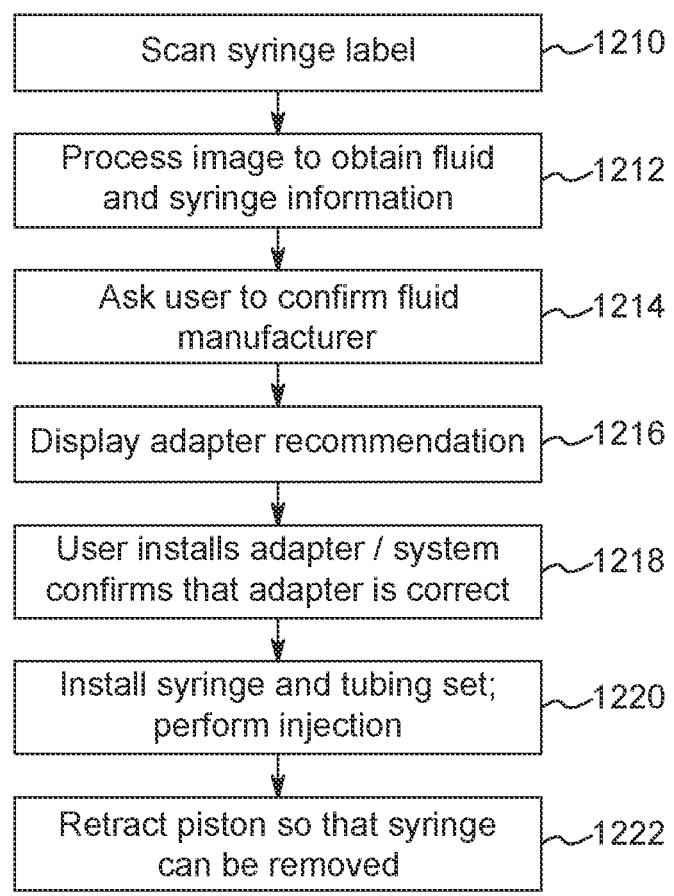
FIG. 22 is a flow chart showing another example process for performing an injection with the injector system in accordance with the present disclosure.

As shown in FIG. 22, a process for automatically identifying the syringe by scanning or recording an image of a syringe label is illustrated. In 1210, a bar code or label of a prefilled syringe is scanned to determine information about the syringe and fluid contained therein. Scanning can be performed using a handheld portable scanner device, such as a bar code scanner. In other examples, an image of the label can be obtained by, for example, taking a picture of the label with a smart phone or similar digital camera device. At 1212, the obtained image or bar code is processed to identify fluid and syringe information. At 1214, a confirmation box may appear on the user interface asking the user to confirm which manufacturer sells the selected contrast fluid and/or to confirm that other information extracted from the label or bar code is correct to identify and confirm that an appropriate fluid is being used for the injection. Once the fluid is identified and confirmed, as shown at 1216, the user interface can provide a recommendation for an adapter to be used. As in previously described examples, an icon can appear on the protocol screen of the user interface indicating to the user a compatible or recommended adapter. The recommended adapter number can also be displayed on the LED display on the front panel of the injector itself. For example, the recommended adapter number can blink or flash on the LED display until a correct adapter is installed or until a predetermined time out period expires. At 1218, the user installs the recommended adapter to the injector and the injector confirms that the adapter is the correct type. At 1220, as in other examples, the prefilled syringe and tubing are installed and the injection is performed. At 1222, following the injection, an injector piston retraction process can be initiated allowing the user to remove the empty syringe from the adapter.

In accordance with further aspects of the present disclosure, in certain instances, health care providers need to be protected from certain liquids administered through a syringe. For example, some diagnostic imaging procedures, such as positron emission tomography (PET) and single-photon emission computed tomography (SPECT) or other nuclear medicine procedures, require that a patient receive radioactive contrast agents, also called radiopharmaceuticals, to obtain images. Illustrative and non-restrictive examples of radiopharmaceuticals include $^{64}$Cu diacetyl-bis (N$^4$-methylthiosemicarbazone) (e.g., ATSM or Copper 64), 18F-fluorodeoxyglucose (FDG), Na$^{18}$F (sodium fluoride), 3'-deoxy-3'-[$^{18}$F]fluorothymidine (FLT), $^{18}$F-fluoromisonidazole (FMISO), gallium, technetium-99m, indium-113m, strontium-87m, and thallium. One method for protecting healthcare providers that come into contact with syringes containing radioactive contrast agents and other radioactive substances is to provide a shield around the body of the syringe. In general, a syringe shield is configured to significantly absorb or block radiation from exiting the syringe and contacting a health care provider during handling and/or administering of the radioactive substance.

Figure 23:
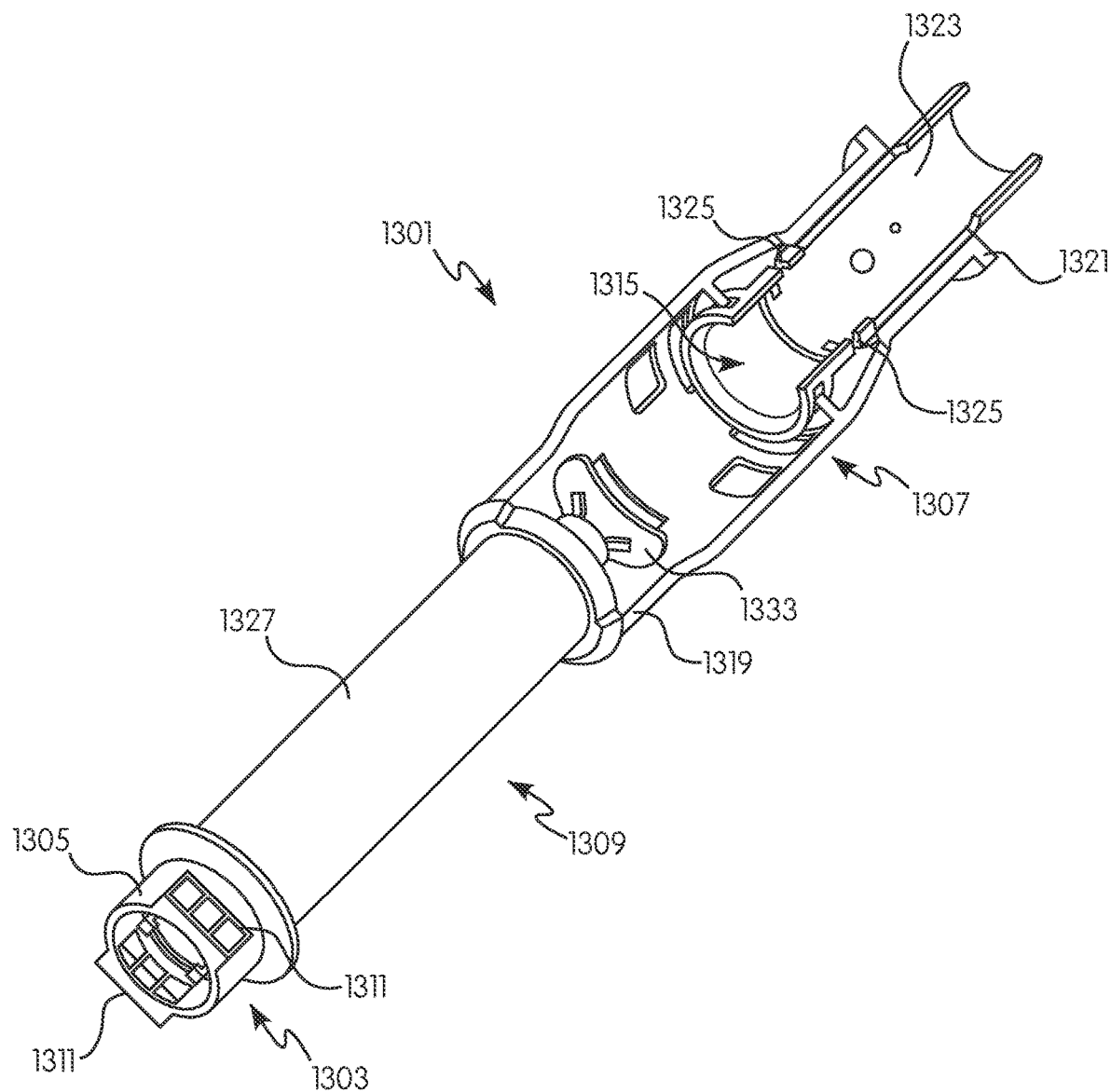
FIG. 23 is a perspective view of an alternative adapter for use with a shielded syringe and the injector system of FIG. 1 in accordance with the present disclosure.
Figure 24:
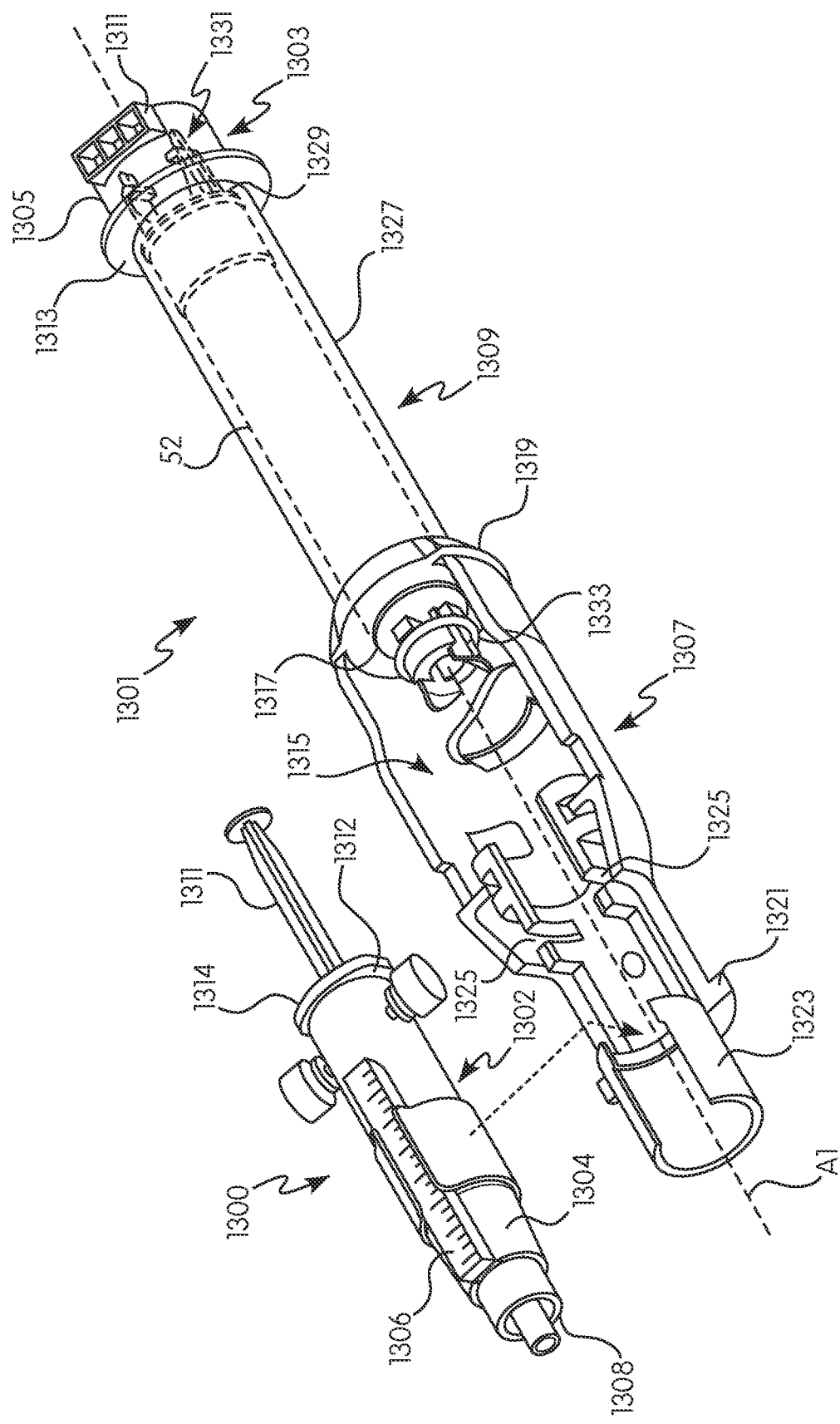
FIG. 24 is an exploded perspective view of the adapter of FIG. 23 and a shielded syringe for positioning therein.
Figure 25:
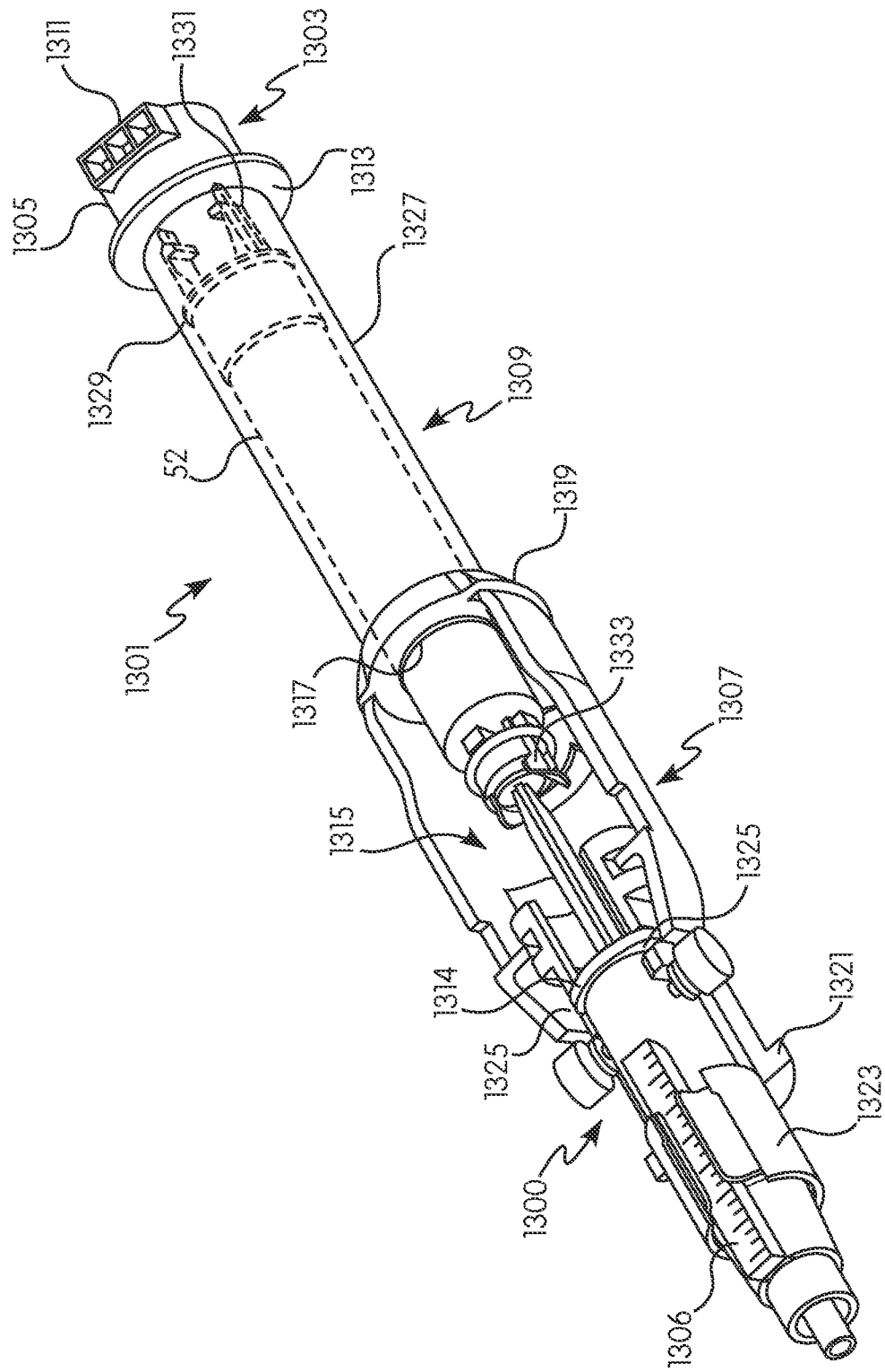
FIG. 25 is a perspective view of the adapter of FIG. 23 with a shielded syringe loaded therein.

With reference to FIGS. 23-25, an adapter 1301 in accordance with the present disclosure may be provided and configured to receive a shielded syringe 1300 and releasably attach the shielded syringe 1300 to the second opening 84 of the injector 10 (See FIG. 1). More specifically and as shown in FIG. 24, a typical shielded syringe 1300 may comprise a syringe body 1302 covered by a syringe shield 1304. A window 1306 may be arranged in the syringe shield 1304 to provide a limited view of the syringe body 1302, such as the injector piston and/or the gradation on the syringe. The syringe body 1302 comprises a forward dispensing end 1308, a plunger rod 1310 slideably positioned within the body 1302, and a flange 1312 extending around a rearward end 1314 of the body 1302.

The syringe shield 1304 may be manufactured out of various materials, including, without limitation, lead, depleted uranium, tungsten, and tungsten impregnated polymers, while the window 1306 may be manufactured out numerous types of materials, including, but not limited to, lead glass or lead loaded acrylic. The syringe shield 1304 may operate to shield a health care provider, particularly the hands of a health care provider, from radiation emanating from radioactive substance contained within the syringe body 1302 as he/she handles, is near, and/or administers the radioactive substance.

In one example, the adapter 1301 comprises: a mounting mechanism 1303 positioned at a rear end 1305 of the adapter 1301 to mount the adapter 1301 in a desired position relative to the front wall 80 of the injector 10; a syringe carrier section 1307 adapted to seat the shielded syringe 1300 therein; and an intermediate section 1309 operably connected to and disposed between the syringe carrier section 1307 and the mounting mechanism 1303.

The mounting mechanism 1303 comprises any suitable mechanism for releasably mounting the adapter 1301 to the syringe interface within the second opening 84. In one example, the mounting mechanism 1303 comprises a pair of mounting flanges 1311 and a drip flange 1313 positioned forward of the mounting flanges 1311 to, for example, facilitate the engagement of the adapter 1301 to the second opening 84 of the injector and/or to prevent fluid expelled from the shielded syringe 1300 from entering into injector 10 via the second opening 84. Additional detail of the mounting mechanism 1303 is provided in U.S. Pat. No. 6,726,657, which is hereby incorporated by reference. However, this type of mounting mechanism is not to be construed as limiting the present disclosure as any suitable mounting mechanism may be utilized.

The syringe carrier section 1307 defines a first opening 1315 on a top thereof to allow placement of the shielded syringe 1300 therein and a second opening 1317 in a rear section 1319 thereof to allow the drive member 40*b* of the injector, as shown for example in FIG. 1, to communicate forward force to the plunger rod 1310 of the shielded syringe 1300. A forward portion 1321 of the syringe carrier section 1307 is designed and configured to support and engage an insert member 1323. The insert member 1323 is designed and configured to securely hold the shielded syringe 1300 therein. The insert member 1323 includes a pair of notches 1325 provided to secure the flange 1312 of the shielded syringe 1300 therein. The notches 1325 abut the flange 1312 such that the force exerted by the shielded syringe 1300 on the adapter 1301 during an injection is generally symmetrical about the axis A1 of the adapter 1301. The adapter 1301 may be such that the forward force on the syringe during injection is transmitted or resisted first by the shield and from the shield to the adapter 1301. Alternatively, the adapter 1301 may interface with one or more aspects of the syringe directly so that the forward force on the syringe is directly transmitted to the adapter 1301, or the force may be transmitted via both force paths as herein described.

The intermediate section 1309 is operably connected to and disposed between the syringe carrier section 1307 and the mounting mechanism 1303. The intermediate section 1309 comprises a cylindrical body 1327 having the push rod 52 at least partially disposed therein. In one example, the push rod 52 has a first end for engaging the plunger rod 1310 of the shielded syringe 1300 and a second end 1329. The second end 1329 of the push rod 52 includes an engagement mechanism 1331 configured to engage the drive member 40*b* of the injector 10. The engagement mechanism 1331 may be the same engagement mechanism 140 shown in FIGS. 3, 4, 11, and 12 or any other suitable engagement mechanism. The first end of the push rod 52 includes a clamping mechanism 1333 configured to releasably connect the push rod 52 to the plunger rod 1310.

In operation of the adapter 1301, the push rod 52 makes a connection with the drive member 40*b* of the injector 10 as described hereinabove after the mounting mechanism 1303 is attached to the front wall 80 of the injector 10. The shielded syringe 1300 can be top loaded via first opening 1315 into syringe carrier section 1307 either before or after connection of adapter 1301 to the injector 10 via the mounting mechanism 1303. The push rod 52 is advanced forward through the intermediate section 1309 by the drive member 40*b* until the clamping mechanism 1333 at the first end thereof engages and connects to the plunger rod 1310. Thereafter, the contents of the shielded syringe 1300 are injected into a patient using the injector 10. As an example, the adapter 1301 may allow an MR injector to controllably deliver a radiopharmaceutical for use in a nuclear medicine imaging procedure.

With reference to FIGS. 26-30, another example of an adapter 1401 for the shielded syringe 1300 is illustrated. The adapter 1401 may for example be used to adapt a CT injector to inject and controllably deliver a nuclear medicine radiopharmaceutical. The adapter 1401 comprises a mounting mechanism 1403 positioned at a rear end of the adapter 1401 to mount the adapter 1401 in a desired position relative to the front wall 80 of the injector 10 (see FIG. 1); a syringe carrier section 1405 adapted to seat the shielded syringe 1300 therein; and an intermediate section 1407 operably connected to and disposed between the syringe carrier section 1405 and the mounting mechanism 1403.

The mounting mechanism 1403 comprises any suitable mechanism for releasably mounting the adapter 1401 to the syringe interface within the second opening 84. In one example, the mounting mechanism 1403 comprises a mounting flange 1409 and a drip flange 1411 positioned forward of the mounting flange 1409 as described in greater detail hereinabove.

The syringe carrier section 1405 includes an opening 1413 on a top thereof to allow placement of the shielded syringe 1300 therein. The rear end of the shielded syringe 1300 includes extension members 1316 configured to engage a rear wall 1415 when a force is applied to the plunger rod 1310 of the shielded syringe 1300.

Figure 26:
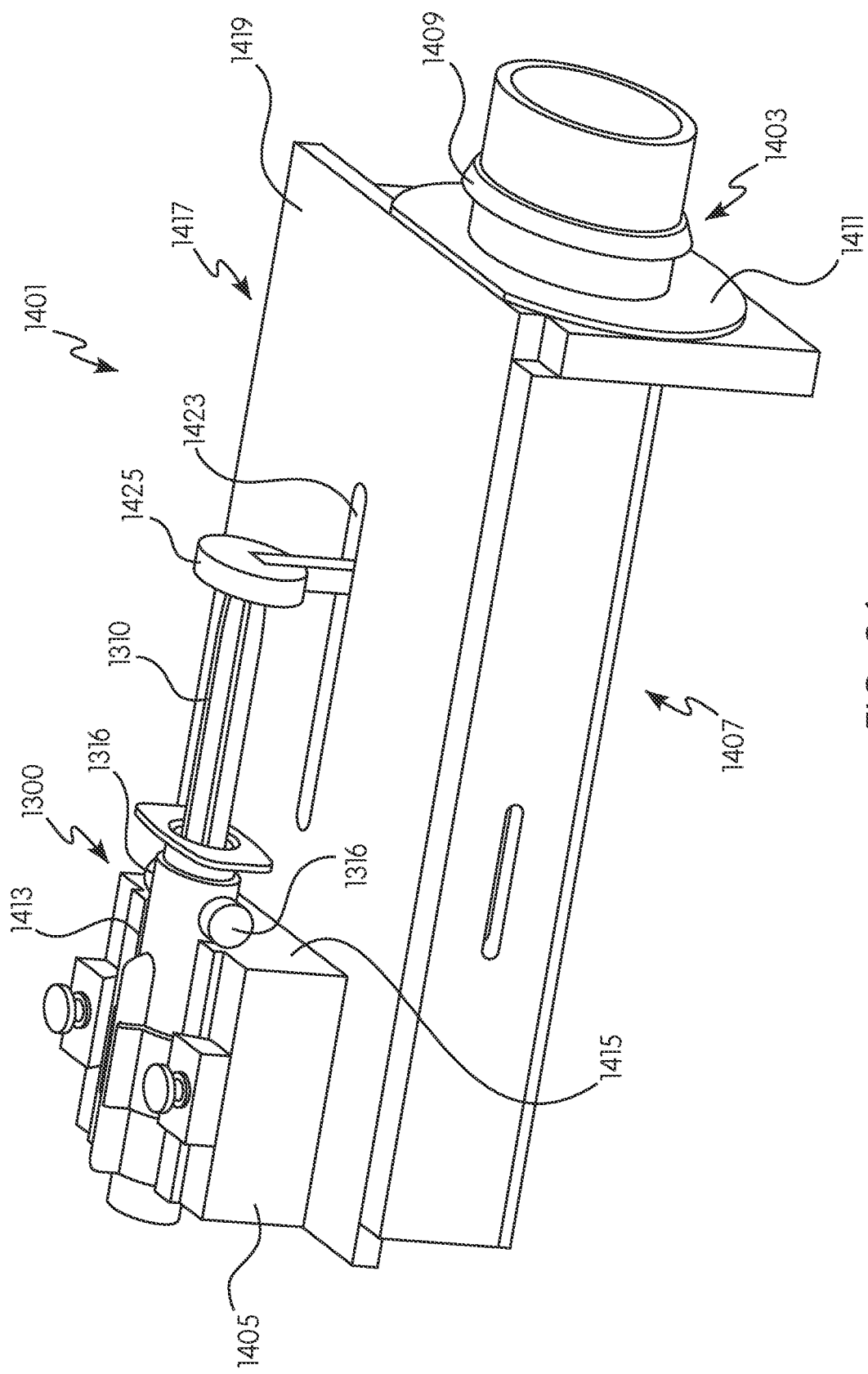
FIG. 26 is a top perspective view of another example of an adapter for use with a shielded syringe and the injector system of FIG. 1 in accordance with the present disclosure.
Figure 27:
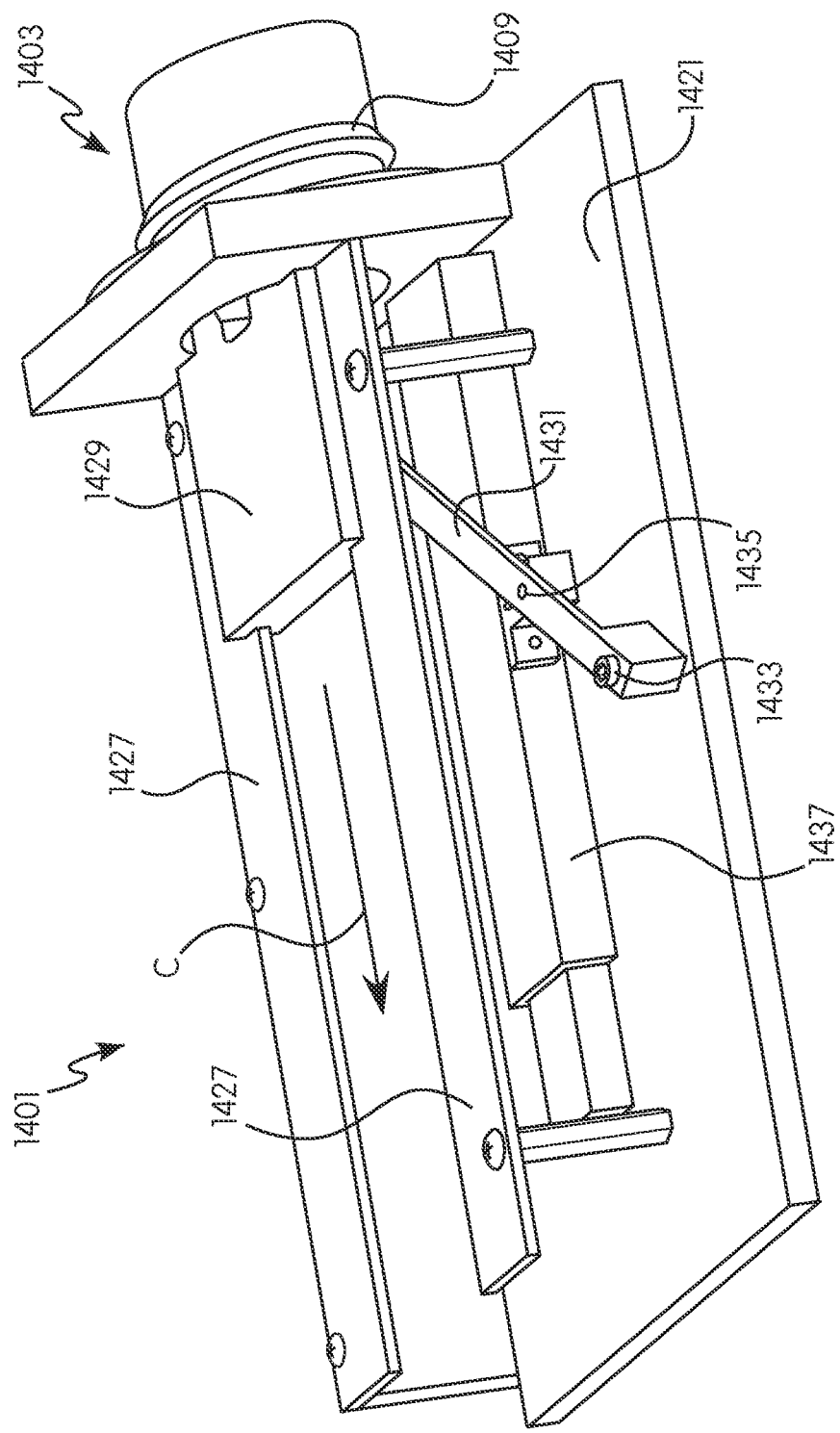
FIG. 27 is a bottom perspective view of the adapter of FIG. 26.
Figure 28:
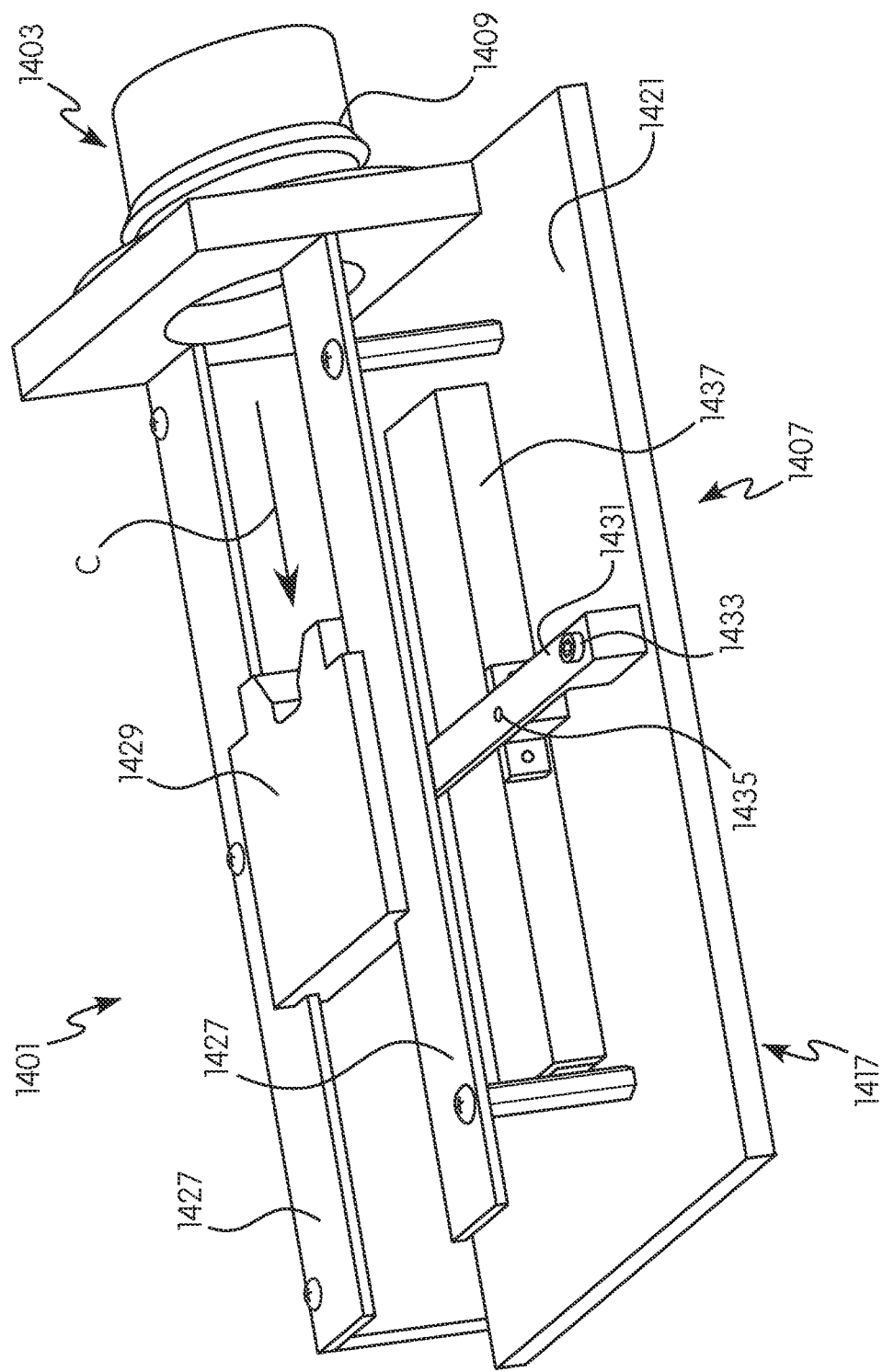
FIG. 28 is a bottom perspective view of the adapter of FIG. 26 illustrating the position of various components once an injection procedure has been commenced.
Figure 29:
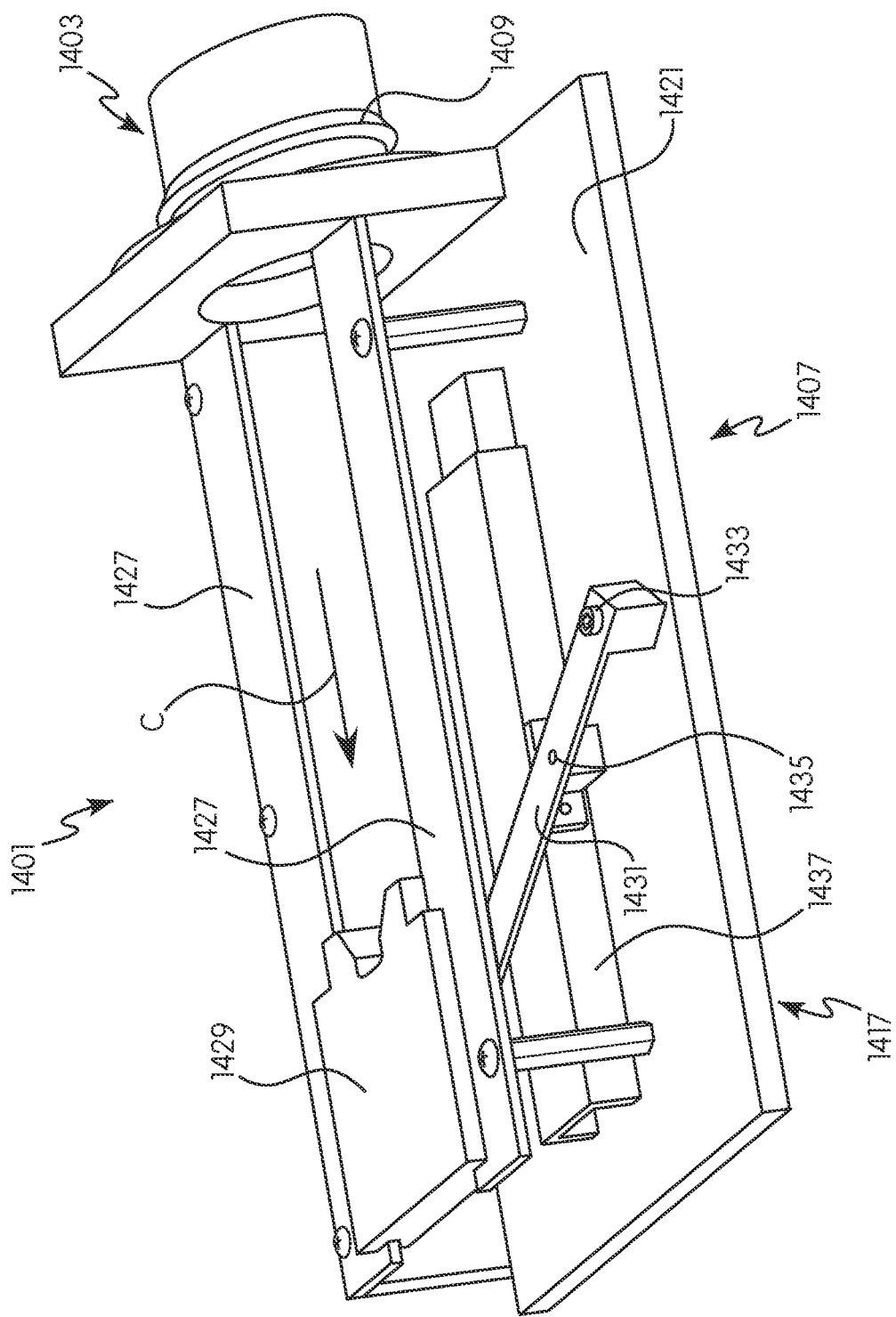
FIG. 29 is a bottom perspective view of the adapter of FIG. 26 illustrating the position of various components once an injection procedure has been completed.
Figure 30:
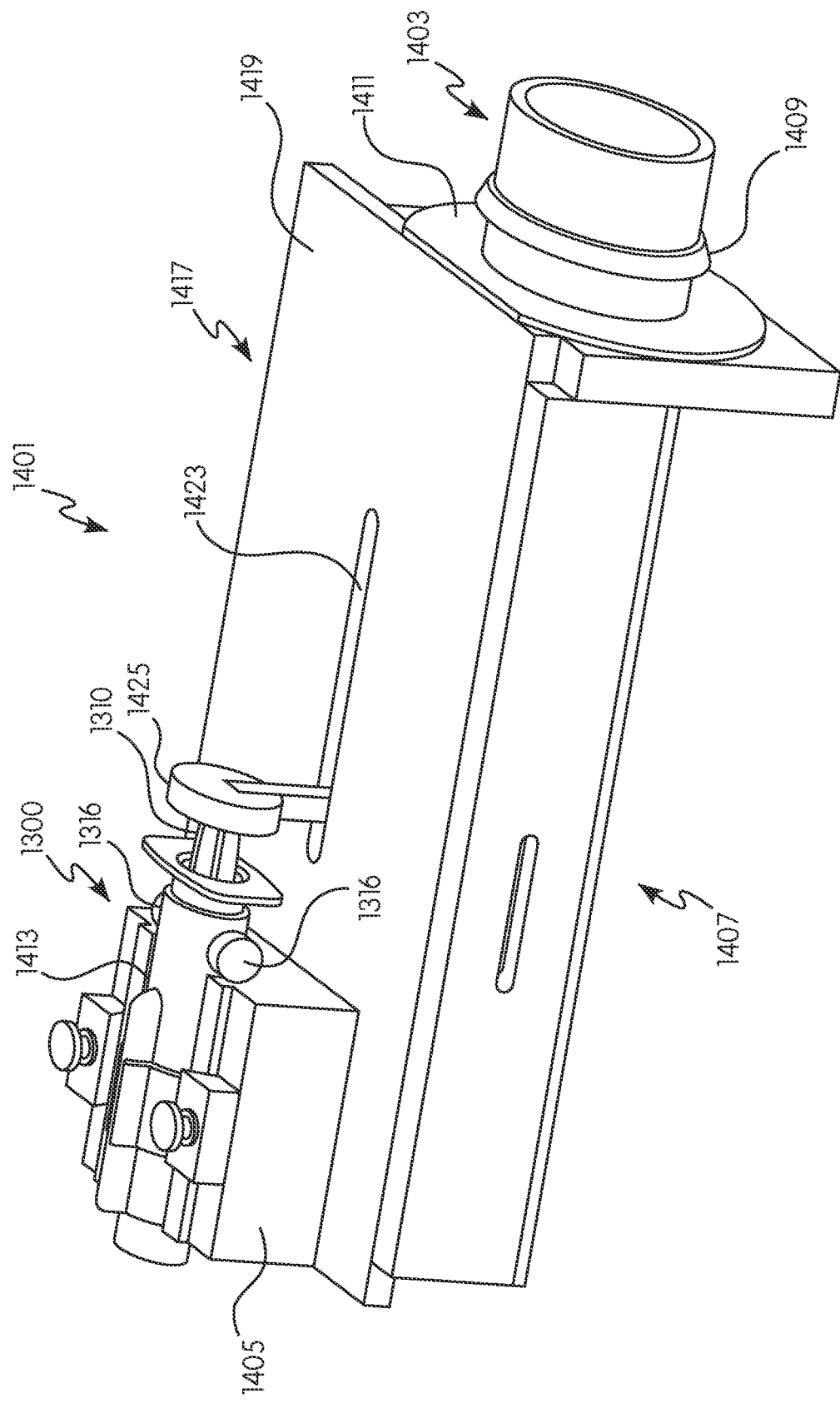
FIG. 30 is a top perspective view of the adapter of FIG. 26 illustrating the position of various components once an injection procedure has been completed.

The intermediate section 1407 comprises a generally planar element 1417 having a top surface 1419 and a bottom surface 1421 and a slot 1423 extending therebetween. A plunger rod engaging mechanism 1425 extends through the slot 1423 and is configured to engage the plunger rod 1310 of the shielded syringe 1300 prior to an injection procedure as shown in FIG. 26. With specific reference to FIG. 27, the bottom surface 1421 of the planar element 1417 includes a pair of rails 1427 extending therefrom. A drive member engaging portion 1429 is provided to engage the drive member 40b (not shown) of the injector 10 and travel along the rails 1427 in the direction of arrow C during an injection procedure. The drive member engaging portion 1429 is operatively connected to a reduction mechanism configured to modify the displacement relationship between the drive member 40b and the plunger rod 1310. More specifically, the drive member engaging portion 1429 is pivotally connected to a first end of a lever 1431. A second end 1433 of the lever 1431 is pivotally connected to bottom surface 1421 of the planar element 1417 and an intermediate portion 1435 of the lever 1431 is pivotally connected to a slider mechanism 1437 located centrally on the bottom surface 1421 of the planar element 1417.

The slider mechanism 1437 is operatively connected to the plunger rod engaging mechanism 1425 such that movement of the slider mechanism 1437 in the direction of arrow C causes the plunger rod 1310 to move through the shielded syringe 1300 and expel fluid therefrom. More specifically, and with reference to FIGS. 28 and 29, as the drive member 40b of the injector 10 (not shown) advances in the direction of arrow C, the drive member 40b (not shown) engages the drive member engaging portion 1429 to advance the drive member engaging portion 1429 along the rails 1427. As the drive member engaging portion 1429 moves along the rails 1427, the lever 1431 pivotally moves relative the drive member engaging portion 1429 and transmits a reduced motion to the slider mechanism 1437 also in the direction of arrow C. As the slider mechanism 1437 moves, this motion is transmitted to the plunger rod engaging mechanism 1425 and the plunger rod 1310 of the shielded syringe 1300, thereby injecting the contents of the shielded syringe 1300 into a patient. In this example, the reduced motion of the slider mechanism 1437 enables more precise and accurate control of the fluid delivery. It may also allow achievement of higher pressures if those are needed. In an alternate example, not shown, the relationship may be reversed and the syringe may have a longer travel than the injector piston can achieve. This mechanical change of piston travel distance with relation to syringe plunger travel distance may be applied to any syringe adapter, not just those with nuclear medicine shields. Moreover, the mechanical change of piston travel may be done with a variety of mechanical assemblies, including for example and without limitation, rack and pinion, ball screws and pulleys.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A feedback and control system for a fluid injector, comprising:
   an injector comprising at least one syringe port configured to receive a syringe adapter configured to receive a syringe therein to operatively connect the syringe to the injector; and
   a control device in electronic communication with the injector, wherein the control device comprises a visual display having a user interface for guiding a user during operation of the injector, the control device being configured to:
   receive information regarding a type of fluid to be injected to a patient;
   determine a recommended adapter type based on the type of fluid to be injected to the patient; and
   provide, on the visual display, an indication of the recommended adapter type to be connected to the at least one syringe port.

2. The feedback and control system of claim 1, wherein the information regarding the type of fluid to be injected to the patient is received by at least one of scanning a bar code on a prefilled syringe intended to be mounted within the syringe adapter, entering information regarding the type of fluid on the user interface, or any combination thereof.

3. The feedback and control system of claim 1, wherein the indication is a visual icon of the recommended adapter type.

4. The feedback and control system of claim 1, wherein the indication of the recommended adapter type to be connected to the at least one syringe port is displayed on a display of the injector.

5. The feedback and control system of claim 1, wherein the control device is further configured to:
   confirm that the syringe adapter mounted to the at least one syringe port is the recommended adapter type; and
   display a notification on the visual display if the syringe adapter mounted to the at least one syringe port is not the recommended adapter type.

6. The feedback and control system of claim 5, wherein the syringe adapter comprises an encoding device associated therewith.

7. The feedback and control system of claim 6, wherein the encoding device is at least one of a bar code having spaced bars, a bar code having raised surfaces representing spaced bars, a slot, a hole, a projection designed to register against a switch on the fluid injector, optically readable devices, a radio frequency identification device (RFID) tag, or any combination thereof.

8. The feedback and control system of claim 6, wherein the at least one syringe port comprises a sensor for obtaining information from the encoding device about the syringe adapter mounted thereto.

9. The feedback and control system of claim 8, wherein the control device confirms that the syringe adapter mounted to the at least one syringe port is the recommended adapter type based on a signal from the sensor for obtaining information from the encoding device associated with the syringe adapter.

10. The feedback and control system of claim 1, where the control device is further configured to:
    determine one or more injection parameters for an injection to be performed based, at least in part, on the recommended adapter type.

11. A method of controlling a fluid injector system comprising an injector comprising at least one syringe port configured to receive a syringe adapter configured to receive a syringe therein to operatively connect the syringe to the injector; and a control device in electronic communication with the injector comprising a visual display having a user interface, the method comprising:
    receiving, by the control device, information regarding a type of fluid to be injected to a patient;
    determining, by the control device, a recommended adapter type based on the type of fluid to be injected to the patient; and
    providing, on the visual display, an indication of the recommended adapter type to be connected to the at least one syringe port.

12. The method of claim 11, wherein the information regarding the type of fluid to be injected to the patient is received by at least one of scanning a bar code on a prefilled syringe intended to be mounted within the syringe adapter, entering the information regarding the type of fluid on the user interface, or any combination thereof.

13. The method of claim 11, wherein the indication is a visual icon of the recommended adapter type.

14. The method of claim 11, further comprising:
mounting the syringe adapter to the at least one syringe port;
confirming that the syringe adapter mounted to the at least one syringe port is the recommended adapter type; and
displaying a notification on the visual display if the syringe adapter mounted to the at least one syringe port is not the recommended adapter type.

15. The method of claim 14, wherein the syringe adapter comprises an encoding device associated therewith.

16. The method of claim 15, wherein the encoding device is at least one of a bar code having spaced bars, a bar code having raised surfaces representing spaced bars, a slot, a hole, a projection designed to register against a switch on the fluid injector, optically readable devices, a radio frequency identification device (RFID) tag, or any combination thereof.

17. The method of claim 15, wherein the at least one syringe port comprises a sensor for obtaining information from the encoding device about the syringe adapter mounted thereto.

18. The method of claim 17, wherein the syringe adapter mounted to the at least one syringe port is confirmed to be the recommended adapter type based on a signal from the sensor for obtaining information from the encoding device associated with the syringe adapter.

19. The method of claim 11, further comprising:
determining, by the control device, one or more injection parameters for an injection to be performed based, at least in part, on the recommended adapter type.

20. A feedback and control system for a fluid injector, comprising:
an injector comprising at least one syringe port configured to receive a syringe adapter configured to receive a syringe therein to operatively connect the syringe to the injector; and
a control device in electronic communication with the injector comprising a visual display having a user interface for guiding a user during operation of the injector, the control device being configured to:
receive information regarding a type of fluid to be injected to a patient determine a recommended adapter type based on the type of fluid to be injected to the patient;
provide, on the visual display, an indication of the recommended adapter type to be connected to the at least one syringe port;
confirm that the syringe adapter mounted to the at least one syringe port is the recommended adapter type; and
display a notification on the visual display if the syringe adapter mounted to the at least one syringe port is not the recommended adapter type.

* * * * *

UNITED STATES PATENT AND TRADEMARK OFFICE
CERTIFICATE OF CORRECTION

PATENT NO. : 11,612,689 B2  
APPLICATION NO. : 17/095450  
DATED : March 28, 2023  
INVENTOR(S) : Bingaman et al.

Page 1 of 2

It is certified that error appears in the above-identified patent and that said Letters Patent is hereby corrected as shown below:

In the Drawings

In Fig. 19, Sheet 14 of 24, for Tag "926", in Line 1, delete "injection?" and insert -- injection --, therefor.

In the Specification

In Column 1, Line 10, delete "2018," and insert -- 2018, now Pat. No. 10,835,668, --, therefor.

In Column 1, Line 12, delete "No." and insert -- Nos. --, therefor.

In Column 7, Line 52, delete "accommodation" and insert -- accommodation of --, therefor.

In Column 13, Line 55, delete "identified" and insert -- identify --, therefor.

In Column 14, Line 46, delete "pounds" and insert -- pound --, therefor.

In Column 20, Line 36, delete "identified" and insert -- identify --, therefor.

In Column 25, Line 16, delete "out" and insert -- out of --, therefor.

In Column 27, Line 26, delete "relative" and insert -- relative to --, therefor.

In the Claims

In Column 28, Line 19, in Claim 4, delete "a" and insert -- the visual --, therefor.

In Column 29, Line 27, in Claim 17, delete "obtaining" and insert -- obtaining the --, therefor.

Signed and Sealed this
Eighth Day of August, 2023

Katherine Kelly Vidal  
*Director of the United States Patent and Trademark Office*

In Column 30, Line 2, in Claim 18, delete "obtaining" and insert -- obtaining the --, therefor.

In Column 30, Line 20, in Claim 20, delete "patient" and insert -- patient; --, therefor.